United States Patent
Igarashi et al.

(10) Patent No.: US 11,517,288 B2
(45) Date of Patent: Dec. 6, 2022

(54) ULTRASONIC DIAGNOSTIC APPARATUS AND IMAGE GENERATING METHOD

(71) Applicant: Toshiba Medical Systems Corporation, Otawara (JP)

(72) Inventors: Yu Igarashi, Kawasaki (JP); Masaki Watanabe, Kawasaki (JP); Yuko Kanayama, Kawasaki (JP); Yasunori Honjo, Kawasaki (JP); Tetsuya Kawagishi, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1170 days.

(21) Appl. No.: 15/159,183

(22) Filed: May 19, 2016

(65) Prior Publication Data

US 2016/0338671 A1   Nov. 24, 2016

(30) Foreign Application Priority Data

May 21, 2015  (JP) .............................. JP2015-103720
May 18, 2016  (JP) .............................. JP2016-099753

(51) Int. Cl.
A61B 8/08  (2006.01)

(52) U.S. Cl.
CPC .......... *A61B 8/5207* (2013.01); *A61B 8/5223* (2013.01); *A61B 8/5238* (2013.01); *A61B 8/5269* (2013.01)

(58) Field of Classification Search
CPC .... A61B 8/5207; A61B 8/5269; A61B 8/5223
See application file for complete search history.

(56) References Cited

U.S. PATENT DOCUMENTS

| | | | |
|---|---|---|---|
| 8,012,090 B2* | 9/2011 | Steen | A61B 8/06 600/407 |
| 2002/0102023 A1* | 8/2002 | Yamauchi | G06K 9/6207 382/199 |
| 2006/0058661 A1* | 3/2006 | Hirama | A61B 8/14 600/437 |
| 2012/0243757 A1* | 9/2012 | Funka-Lea | G06T 7/0002 382/131 |
| 2015/0002538 A1 | 1/2015 | Sohn et al. | |

FOREIGN PATENT DOCUMENTS

| | | |
|---|---|---|
| JP | 2010-207492 | 9/2010 |
| JP | 2013-223792 | 10/2013 |

OTHER PUBLICATIONS

"Automatic Shadow Detection in Intra Vascular Ultrasound Images Using Adaptive Thresholding" by M. Basij et al. IEEE Int. Conf. Systems, Man, Cybernetics. Oct. 2012 (Year: 2012).*

(Continued)

*Primary Examiner* — Jason M Ip

(74) *Attorney, Agent, or Firm* — Oblon, McClelland, Maier & Neustadt, L.L.P.

(57) ABSTRACT

An ultrasonic diagnostic apparatus in an embodiment includes processing circuitry. The processing circuitry is configured to cause an ultrasonic probe to perform an ultrasound scan of a subject. The processing circuitry is configured to generate a shadow image by assigning at least one of hue, saturation, and lightness depending on a feature of an acoustic shadow that has appeared in the result of the ultrasound scan.

17 Claims, 16 Drawing Sheets

(56) References Cited

OTHER PUBLICATIONS

"Detection and Quantification of Calcifications in Intravascular Ultrasound Images by Automatic Thresholding" by E. S. Filho et al. Ultrasound in Med. & Biol. vol. 34, No. 1, pp. 160-165 (Year: 2008).*

Office Action dated Feb. 12, 2020 in Japanese Application No. 2016-099753, filed May 18, 2016.

* cited by examiner

ULTRASONIC DIAGNOSTIC APPARATUS AND IMAGE GENERATING METHOD

CROSS-REFERENCE TO RELATED APPLICATIONS

This application is based upon and claims the benefit of priority from Japanese Patent Application No. 2015-103720, filed on May 21, 2015 and Japanese Patent Application No. 2016-099753, filed on May 18, 2016; the entire contents of which are incorporated herein by reference.

FIELD

Embodiments described herein relate generally to an ultrasonic diagnostic apparatus and an image generating method.

BACKGROUND

Conventionally, in ultrasonic images, there have been cases in which an acoustic artifact that Is characteristic of ultrasonic waves arises. For example, because ultrasonic waves are intensely reflected by a hard tissue, the ultrasonic waves reflected at a position deeper than the hard tissue are weakened and an acoustic shadow (hereinafter referred to as shadow) that is darkly indicated in an image may arise. Such a shadow may arise not only at hard tissues such as bones but also at a tissue that is locally indurated by diseases such as diffuse liver disease. In such a case, pectinate shadows may appear in the image, for example.

DETAILED DESCRIPTION

According to an embodiment, an ultrasonic diagram apparatus includes processing circuitry. The processing circuitry is configured to cause an ultrasonic probe to perform an ultrasound scan of a subject. The processing circuitry is configured to generate a shadow image by assigning at least one of hue, saturation, and lightness depending on a feature of an acoustic shadow that has appeared in a result of the ultrasound scan.

With reference to the accompanying drawings, the following describes in detail exemplary embodiments of an ultrasonic diagnostic apparatus and an image generating method. In the following description, for the same constituent elements, common reference signs are given to and redundant explanations thereof are omitted.

First Embodiment

Figure 1:
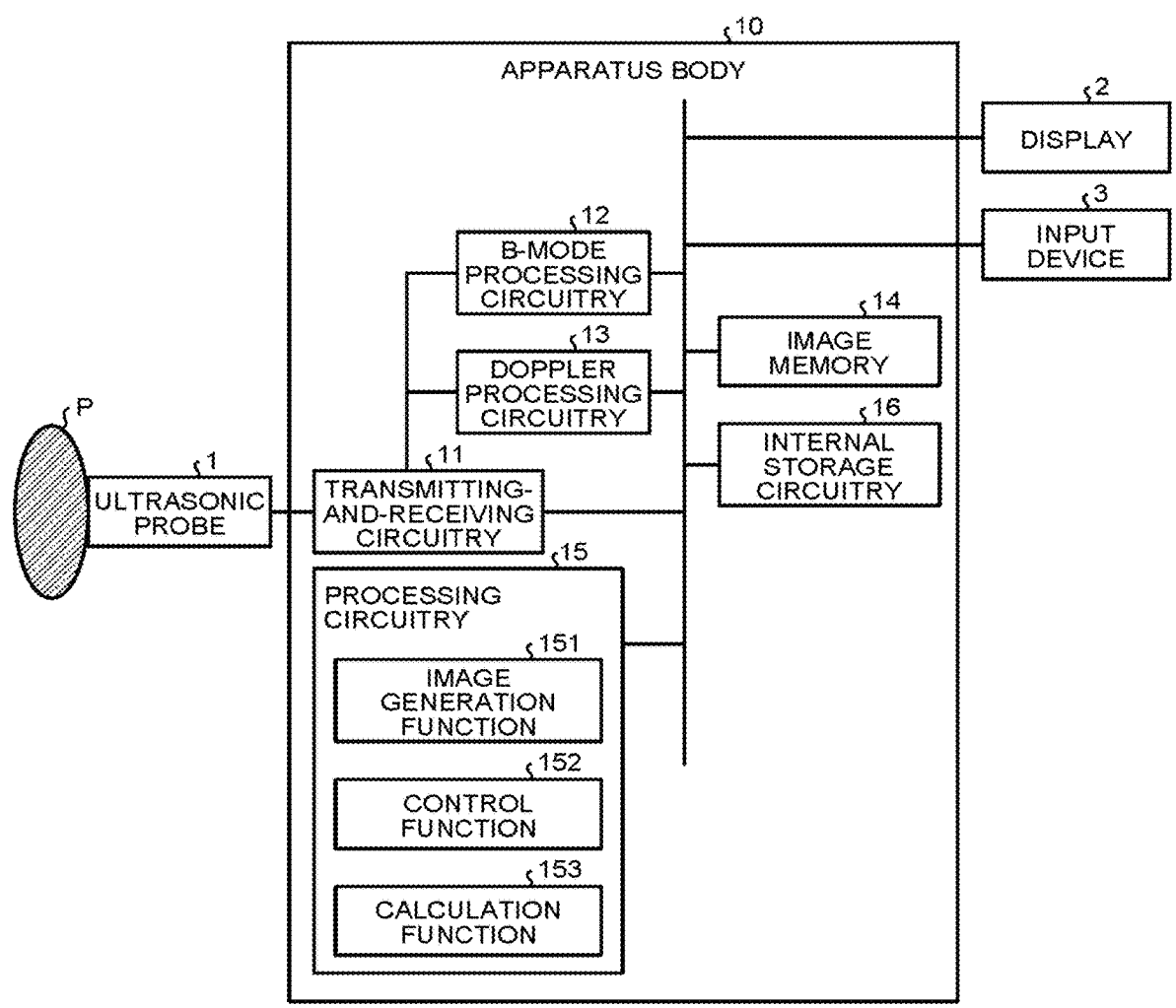
FIG. 1 is a block diagram illustrating an example of the configuration of an ultrasonic diagnostic apparatus according to a first embodiment.

First, the configuration of an ultrasonic diagnostic apparatus according to a first embodiment will be described. FIG. 1 is a block diagram illustrating an example of the configuration of the ultrasonic diagnostic apparatus in the first embodiment. As illustrated in FIG. 1, the ultrasonic diagnostic apparatus in the first embodiment includes an ultrasonic probe 1, a display 2, an input unit 3, and an apparatus body 10.

The ultrasonic probe 1 includes a plurality of piezoelectric transducer elements, and these piezoelectric transducer elements generate ultrasonic waves based on a drive signal supplied from later-described transmitting-and-receiving circuitry 11 that the apparatus body 10 includes, for example. The ultrasonic probe 1 receives reflected waves from a subject P and converts the received reflected waves into an electrical signal. The ultrasonic probe 1 further includes a matching layer that is provided on the piezoelectric transducer elements, a backing material that prevents ultrasonic waves from propagating toward the rear from the piezoelectric transducer elements, and others. The ultrasonic probe 1 is detachably connected to the apparatus body 10.

When ultrasonic waves are transmitted to the subject P from the ultrasonic probe 1, the transmitted ultrasonic waves are reflected by discontinuous planes in acoustic impedance in body tissue of the subject F one after another, and are received by the piezoelectric transducer elements of the ultrasonic probe 1 as a reflected wave signal. The amplitude of the reflected wave signal received is dependent on the difference in acoustic impedance at the discontinuous plane by which the ultrasonic waves are reflected. The reflected wave signal, when transmitted ultrasonic pulses are reflected by blood flow, the surface of a heart wall, and others that are in motion, undergoes frequency deviation that is dependent on the velocity component of a moving body with respect to the transmitting direction of the ultrasonic waves by the Doppler effect.

The ultrasonic probe 1 in the first embodiment may be an ultrasonic probe that is capable of scanning the subject P in two-dimension by ultrasonic waves and of scanning the subject P in three-dimension. Specifically, the ultrasonic probe 1 in the first embodiment may be a mechanical 4D probe that scans the subject P in two-dimension by a plurality of piezoelectric transducer elements arrayed in a single row and scans the subject P in three-dimension by swinging the piezoelectric transducer elements at a certain angle (swing angle), and may be a 2D probe that is capable of performing an ultrasound scan on the subject P in three-dimension by arraying a plurality of piezoelectric transducer elements in a matrix. The 2D probe is further capable of scanning the subject P in two-dimension by focusing and transmitting the ultrasonic waves. The ultrasound scan in the first embodiment indicates that data for one frame is collected by at least one time of transmitting and receiving ultrasonic waves.

The input unit 3 includes a mouse, a keyboard, buttons, panel switches, a touch command screen, a foot switch, a trackball, a joystick, and others, receives various setting requests from an operator of the ultrasonic diagnostic apparatus, and transfers the received various setting requests to the apparatus body 10. For example, the input unit 3 receives a request of setting a region of interest (ROI) for an ultrasonic image.

The display 2 displays a graphical user interface (GUI) for the operator of the ultrasonic diagnostic apparatus to input various setting requests by using the input unit 3, and displays a variety of image data and others generated in the apparatus body 10.

The apparatus body 10 is a device that generates ultrasonic image data based on the reflected wave signal received by the ultrasonic probe 1. For example, the apparatus body 10 in the first embodiment is a device capable of generating two-dimensional ultrasonic image data based on two-dimensional reflected wave data received by the ultrasonic probe 1. Furthermore, the apparatus body 10 in the first embodiment is a device capable of generating three-dimensional ultrasonic image data based on three-dimensional reflected wave data received by the ultrasonic probe 1, for example.

The apparatus body 10, as illustrated in FIG. 1, includes the transmitting-and-receiving circuitry 11, B-mode processing circuitry 12, Doppler processing circuitry 13, an image memory 14, processing circuitry 15, and internal storage circuitry 16. In the ultrasonic diagnostic apparatus illustrated in FIG. 1, various processing functions are stored in the internal storage circuitry 16 in a form of computer programs that are executable by a computer. The transmitting-and-receiving circuitry 11, the B-mode processing circuitry 12, the Doppler processing circuitry 13, and the processing circuitry 15 are processors that implement functions corresponding to various computer programs by reading out an appropriate computer program from the internal storage circuitry 16 and executing the read computer program. In other words, the various circuitry in a state of having read out the respective computer programs are to have the function corresponding to the computer program that has been read out.

The term "processor" used in the above description means a central processing unit (CPU), a graphics processing unit (GPU), or a circuit such as an application specific integrated circuit (ASIC), a programmable logic device (for example, a simple programmable logic device (SPLD) and a complex programmable logic device (CPLD)), and a field programmable gate array (FPGA), for example. The processor implements the function by reading out the computer program stored in the storage circuitry and executing the read computer program. It does not matter even if it is configured such that, in place of storing the computer program in the storage circuitry, the computer program is incorporated directly in circuitry of the processor. In this case, the processor implements the function by reading out the computer program incorporated in the circuitry and executing the read computer program. Each processor in the first embodiment is not limited to a processor configured as a single circuit, and may be configured to implement its function by combining a plurality of independent circuits as a single processor.

The transmitting-and-receiving circuitry 11 includes a pulse generator, a transmission delay circuitry, a pulsar, and others, and supplies a drive signal to the ultrasonic probe 1. The pulse generator repeatedly generates rate pulses to form transmission ultrasonic waves at a certain rate frequency. The transmission delay circuitry gives, to each of the rate pulses generated by the pulse generator, a delay time that is necessary for each of the piezoelectric transducer elements to focus the ultrasonic waves generated from the ultrasonic probe 1 into a beam shape and to determine the transmission directivity. The pulsar applies the drive signal (drive pulses) to the ultrasonic probe 1 at the timing based on the rate pulses. That is, the transmission delay circuitry arbitrarily adjusts the transmission direction of the ultrasonic waves transmitted from the plane of the piezoelectric transducer elements by varying the delay time given to the respective rate pulses.

The transmitting-and-receiving circuitry 11 has a function capable of instantly changing a transmission frequency, a transmission drive voltage, and others in order to execute a certain scan sequence based on the instructions of the processing circuitry 15 which will be described later. In particular, the change in the transmission drive voltage is implemented by an oscillator circuitry of a linear amplifier type that can instantly switch the value thereof or by a mechanism that electrically switches a plurality of power supply units.

The transmitting-and-receiving circuitry 11 further includes a pre-amplifier, an analog-to-digital (A/D) converter, reception delay circuitry, an adder, and others, and generates reflected wave data by performing a variety of processing on the reflected wave signal received by the ultrasonic probe 1. The pre-amplifier amplifies the reflected wave signal for each channel. The A/D converter performs A/D conversion on the amplified reflected wave signal. The reception delay circuitry gives a delay time necessary to determine the reception directivity. The adder performs addition processing of the reflected wave signal that has been processed by the reception delay circuitry and generates the reflected wave data. By the addition processing of the adder, the reflection component of the reflected wave signal from the direction corresponding to the reception directivity is emphasized, and by the reception directivity and the transmission directivity, an overall beam of ultrasonic transmission and reception is formed.

The transmitting-and-receiving circuitry 11 in the first embodiment, in order to perform two-dimensional scanning of the subject P, transmits a two-dimensional ultrasonic beam from the ultrasonic probe 1. The transmitting-andreceiving circuitry 11 in the first embodiment then generates two-dimensional reflected wave data from a two-dimensional reflected wave signal received by the ultrasonic probe 1. Furthermore, the transmitting-and-receiving circuitry 11 in the first embodiment, in order to perform three-dimensional scanning of the subject P, transmits a three-dimensional ultrasonic beam from the ultrasonic probe 1. The transmitting-and-receiving circuitry 11 in the first embodiment then generates three-dimensional reflected wave data from a three-dimensional reflected wave signal received by the ultrasonic probe 1.

The form of the output signal from the transmitting-and-receiving circuitry 11 is selectable from various forms such as a case of a signal referred to as a radio frequency (RF) signal in which phase information is included and a case of amplitude information after envelope detection processing, for example.

The B-mode processing circuitry 12 receives the reflected wave data from the transmitting-and-receiving circuitry 11, performs the processing of logarithmic amplification, envelope detection, and others, and generates data (B-mode data) in which the signal intensity is expressed by the brightness of luminance.

The Doppler processing circuitry 13 performs frequency analysis of velocity information on the reflected wave data received from the transmitting-and-receiving circuitry 11, extracts blood flow, tissue, and echo components of contrast agent by the Doppler effect, and generates data (Doppler data) in which moving body information such as velocity, dispersion, and power has been extracted on multi-points. The moving body in the first embodiment is fluid such as blood flowing in blood vessels, lymph flowing in lymph vessels, and others.

The B-mode processing circuitry 12 and the Doppler processing circuitry 13 in the first embodiment can perform processing on both two-dimensional reflected wave data and three-dimensional reflected wave data. That is, the B-mode processing circuitry 12 generates two-dimensional B-mode data from two-dimensional reflected wave data and generates three-dimensional B-mode data from three-dimensional reflected wave data. The Doppler processing circuitry 13 generates two-dimensional Doppler data from two-dimensional reflected wave data and generates three-dimensional Doppler data from three-dimensional reflected wave data. The three-dimensional B-mode data is the data to which a luminance value corresponding to the reflection intensity of a reflection source located at each of a plurality of points (sample points) defined on each scanning line within a three-dimensional scan range is assigned. The three-dimensional Doppler data is the data to which a luminance value corresponding to the value of blood flow information (velocity, dispersion, power) to each of a plurality of points (sample points) defined on each scanning line within a three-dimensional scan range is assigned.

The image memory 14 is a memory storing therein image data for display generated by the processing circuitry 15 which will be described later. The image memory 14 is further capable of storing therein the data generated by the B-mode processing circuitry 12 and the Doppler processing circuitry 13. The B-mode data and the Doppler data stored in the image memory 14 can be called up by the operator after diagnosis, and via the processing circuitry 15, are made into ultrasonic image data for display, for example.

The internal storage circuitry 16 stores therein control computer programs to perform ultrasonic transmission and reception, image processing, and display processing; and a variety of data such as diagnostic information (for example, patient ID and doctor's findings), diagnosis protocols, and various body marks. The internal storage circuitry 16 is used also for the storage of the image data that the image memory 14 stores therein, as necessary. The data stored in the internal storage circuitry 16 can be transferred to an external device via an interface not depicted.

The processing circuitry 15 controls the overall processing of the ultrasonic diagnostic apparatus Specifically, the processing circuitry 15 performs various processing by reading out the computer programs corresponding to an image generation function 151 and executing the read computer programs, a control function 152, and a calculation function 153 illustrated in FIG. 1, from the internal storage circuitry 16. For example, based on various setting requests received from the operator via the input unit 3 and on various control computer programs and a variety of data read in from the internal storage circuitry 16, the processing circuitry 15 controls the processing of the transmitting-and-receiving circuitry 11, the B-mode processing circuitry 12, and the Doppler processing circuitry 13. Furthermore, the processing circuitry 15 performs control so that the ultrasonic image data for display stored in the image memory 14 and the internal storage circuitry 16 is displayed on the display 2. The processing circuitry 15 further performs control so that the processing result of the image generation function 151 is displayed on the display 2. For example, the processing circuitry 15 reads out the computer program corresponding to the control function 152 and executes the read computer program, and thereby performs the overall control of the apparatus and controls the processing as in the foregoing. The image generation function 151 and the calculation function 153 are also referred to as processors. The control function 152 is also referred to as a controller.

The image generation function 151 generates ultrasonic image data from the data generated by the B-mode processing circuitry 12 and the Doppler processing circuitry 73. That is, the image generation function 151 generates B-mode image data that represents the intensity of reflected waves in luminance from the two-dimensional B-mode data generated by the B-mode processing circuitry 12. The B-mode image data is the data in which a tissue form within an area on which the ultrasound scan has been performed is visualized. Furthermore, the image generation function 151 generates Doppler image data that represents the moving body information from the two-dimensional Doppler data generated by the Doppler processing circuitry 13. The Doppler image data is velocity image data, dispersion image data, power image data, or image data of the combination of the foregoing. The Doppler data is the data representing fluid information concerning the fluid that flows in an area on which the ultrasound scan has been performed.

The image generation function 151, in general, converts the rows of scanning line signal of the ultrasound scan into the rows of scanning line signal of a video format typified by television and others scan conversion), and generates ultrasonic image data for display. Specifically, the image generation function 151 performs coordinate conversion according to the scanning form of ultrasonic waves by the ultrasonic probe 1, and thereby generates the ultrasonic image data for display. The image generation function 151, as a variety of image processing other than the scan conversion, by using a plurality of image frames after scan conversion, further performs image processing (smoothing processing) to regenerate a mean-value image of luminance and image processing (edge enhancement processing) that uses a differential filter within the images, for example. Furthermore, the image generation function 151 combines ultrasonic image data with character information on various parameters, scales, body marks, and others.

That is, the B-mode data and the Doppler data are ultrasonic image data before scan conversion processing, and the data that the image generation function 151 generates is the ultrasonic image data for display after scan conversion processing. The B-mode data and the Doppler data are also referred to as raw data.

Furthermore, the image generation function 151 performs coordinate conversion on the three-dimensional B-mode data generated by the B-mode processing circuitry 12, and thereby generates three-dimensional B-mode image data. The image generation function 151 further perform coordinate conversion on the three-dimensional Doppler data generated by the Doppler processing circuitry 13, and thereby generates three-dimensional Doppler image data. The three-dimensional B-mode data and the three-dimensional Doppler data are volume data before scan conversion processing. That is, the image generation function 151 generates "three-dimensional B-mode image data and three-dimensional Doppler image data" "volume data that is three-dimensional ultrasonic image data."

Moreover, the image generation function 151 performs rendering processing on volume data so as to generate a variety of two-dimensional image data to display the volume data on the display 2. The rendering processing performed by the image generation function 151 includes the processing generating MDR image data from the volume data by performing multi-planar reconstruction (MPR). The rendering processing performed by the image generation function 151 further includes the processing of performing "curved MPR" on the volume data and the processing of performing "maximum intensity projection" on the volume data. The rendering processing performed by the image generation function 151 further includes volume rendering (VR) processing that generates two-dimensional image data in which three-dimensional information has been reflected.

The image generation function 151 further generates a variety of information based on a calculation result by the calculation function 153 which will be described later. Specifically, the image generation function 151 generates a shadow image based on the calculation result, and generates information indicative of measurement result concerning shadows. The shadow image and the information indicative of measurement result will be described later.

The control function 152 performs the above-described various control in the whole of the apparatus. Furthermore, the control function 152 causes the display 2 to display thereon the shadow image and the information indicative of measurement result that are generated by the image generation function 151. The calculation function 153 generates shadow information based on the result of an ultrasound scan. The processing performed by the calculation function 153 will be described later in detail.

As in the foregoing, the overall configuration of the ultrasonic diagnostic apparatus in the first embodiment has been explained. Under such a configuration, the ultrasonic diagnostic apparatus the first embodiment makes it possible to perform the extraction of shadows in an ultrasonic image accurately. As in the foregoing, in the ultrasonic image, an acoustic shadow (shadow) that is darkly indicated at a position deeper than a disease site may arise, for example. When the characteristics of tissue are changed by hepatic cirrhosis, fatty liver, and others, for example, the shadow may arise. Thus, if the shadow in the ultrasonic image can be accurately extracted, it is conceivable that the diagnostic performance by ultrasonic image can be improved.

Figure 2:
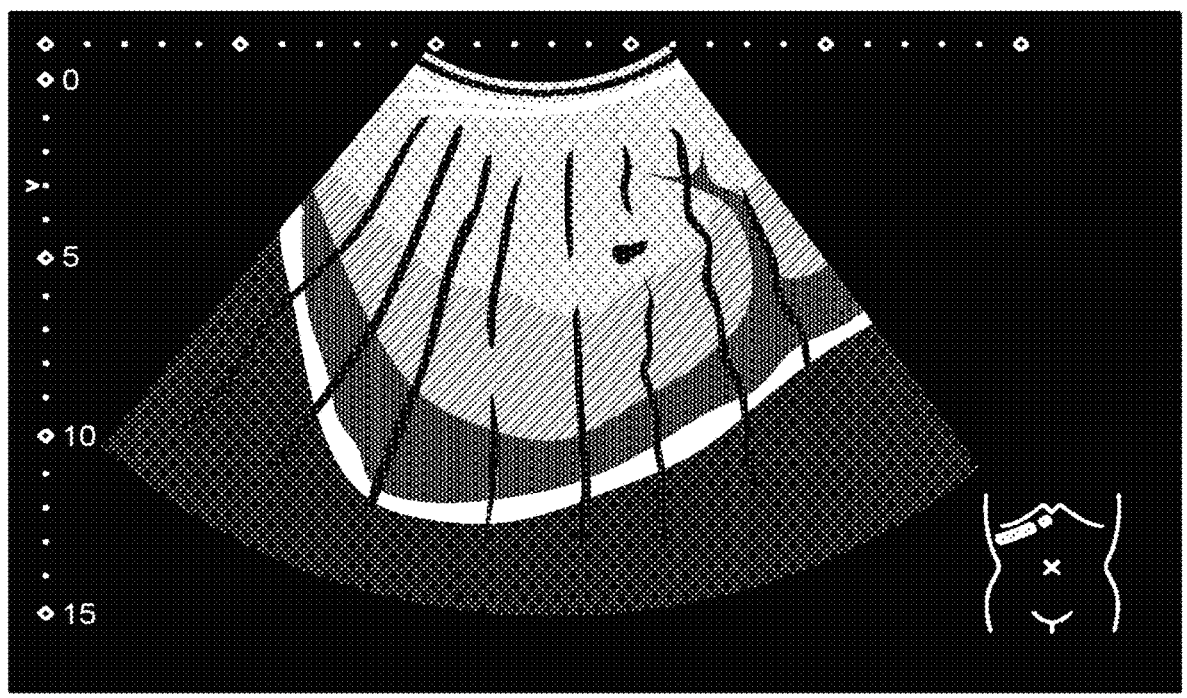
FIG. 2 is a diagram illustrating one example of an ultrasonic image including shadows in the first embodiment.

FIG. 2 is a diagram illustrating one example of an ultrasonic image in the first embodiment. In FIG. 2, an ultrasonic image of a liver is illustrated. For example, as illustrated in FIG. 2, in the ultrasonic image of a liver, pectinate shadows that appear as black streaks running toward the lower side from the upper side of the image may arise. From such an ultrasonic image, it is expected that, if the shadows can be extracted quantitatively, it also becomes possible to diagnose what kind of disease is involved, for example. Consequently, the ultrasonic diagnostic apparatus in the first embodiment makes it possible to accurately extract the shadows in the ultrasonic image by the processing performed by the processing circuitry 15 which will be described in detail in the following.

The control function 152 illustrated in FIG. 1 causes the ultrasonic probe 1 to perform an ultrasound scan of the subject. The calculation function 153 illustrated in FIG. 1 then analyzes the result of the ultrasound scan for each depth, and generates shadow information that is information concerning the acoustic shadows that have appeared in the result of the ultrasound scan based on the result of the analysis on a plurality of depths. Specifically, the calculation function 153 analyzes signals collected by the ultrasound scan for each depth, and extracts shadows included in the ultrasonic image. That is, the calculation function 153 analyzes the signals in an orientation direction (lateral direction) and extracts the shadows.

Figure 3A:
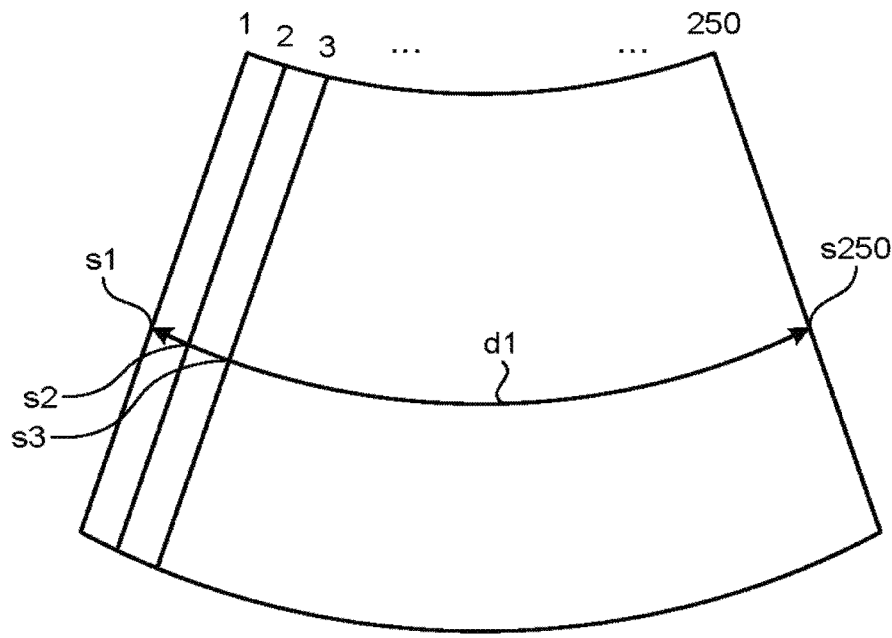
FIG. 3A is a diagram for explaining a processing object of a calculation function in the first embodiment.
Figure 3B:
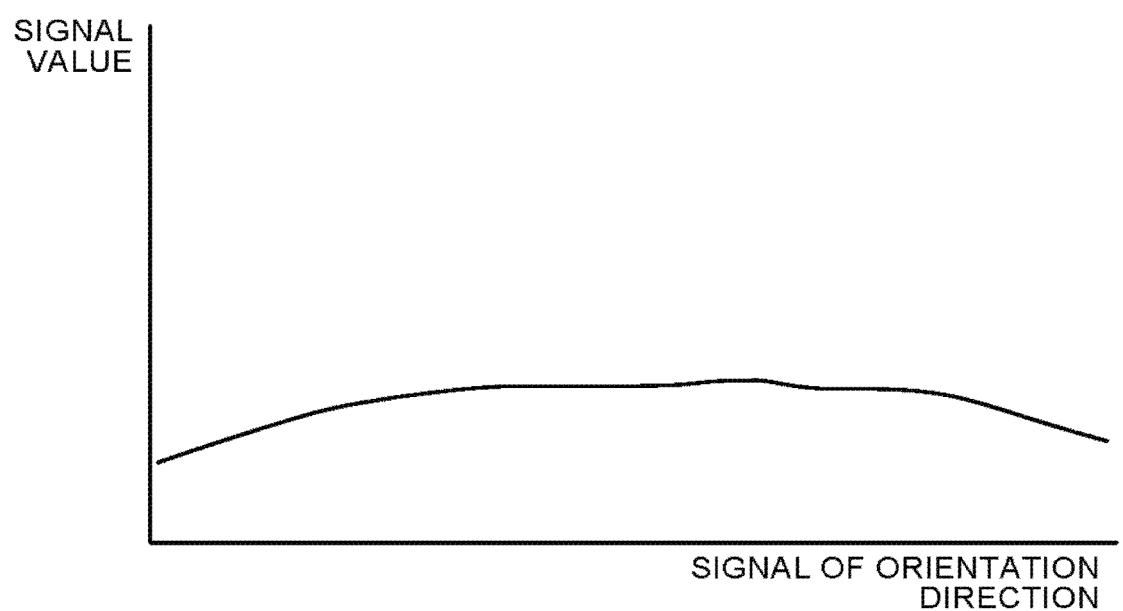
FIG. 3B is a diagram for explaining the processing object of the calculation function in the first embodiment.

FIGS. 3A and 3B are diagrams for explaining a processing object of the calculation function 153 in the first embodiment. In FIG. 3A, scanning lines in an ultrasonic image are illustrated. In FIG. 3B, illustrated is a graphic chart with the ordinate axis representing a signal value and the abscissa axis representing signals of the orientation direction (scanning lines). For example, the calculation function 153, as illustrated in FIG. 3A, analyzes each of signal values "s1" to "s250" at a depth of "d1" of scanning lines "1" to "250" at the time an ultrasound scan is performed. In one example, the calculation function 153 extracts the signal values "s1" to "s250" at the depth of "d1", and calculates fluctuation in the signal values of the orientation direction for each depth. For example, the calculation function 153, as illustrated in FIG. 3B, extracts the signal value at the depth of "d1" for each of the scanning lines, generates a graphic chart with the abscissa axis as the scanning line and with the ordinate axis as the signal value, and extracts shadows based on the generated graphic chart. While only the depth "d1" is illustrated in FIGS. 3A and 3B, the calculation function 153, in practice, analyzes the signals of the orientation direction for each depth corresponding to all sample points on the scanning lines. For example, the calculation function 153 performs analysis at locations shallower than the depth "d1" illustrated in FIG. 3A and at locations deeper than that.

The signal value handled by the calculation function 153 can be any desired signal. Examples of the signal value handled by the calculation function 153 may include reflected wave data on which addition processing has been performed by the adder of the transmitting-and-receiving circuitry 11, amplitude data after envelop detection processing, or a luminance value. In the following description, a situation in which amplitude data or a luminance value is used is exemplified as one example.

As in the foregoing, when the signal values for each depth are extracted, the calculation function 153 analyzes the extracted signal values, and thereby generates the shadow information. For example, the calculation function 153, at least as a part of the analysis performed for each depth, performs at least one of a comparison between a certain threshold and the signal value of each signal at an identical depth obtained by the ultrasound scan and a comparison between a certain threshold and the difference between the signal value of each signal obtained at an identical depth obtained by the ultrasound scan and a reference value, and thereby generates the shadow information. The above-described reference value is a signal value of the signal adjacent to each signal at an identical depth, for example.

In one example, the calculation function 153 generates the shadow information by extracting at least any of the signal that falls below a certain threshold in the signals for each depth (each signal at an identical depth) collected by the ultrasound scan and the signal for which the difference between adjacent signals for each depth exceeds a certain threshold. For example, the calculation function 153 extracts as a shadow, in the graphic chart of the signal value illustrated in FIG. 3B, the location of the scanning line the signal value of which falls below a certain threshold. The calculation function 153 further extracts as a shadow, in the graphic chart of the signal value illustrated in FIG. 3B, the location of the scanning line for which the difference between adjacent signals exceeds a certain threshold. In the case of comparing the certain threshold with the difference between signals, it may be a case of comparing the certain threshold with the difference not only between adjacent signals but also between signals not being adjacent. For example, it may be a case of comparing the certain threshold with the difference between the signal indicating a maximum value and the signal indicating a minimum value, out of a plurality of signals that are within a certain range at an identical depth. The calculation function 153 can use the above-described two shadow extraction methods independently or in combination. In FIG. 3E, because the chart is schematically illustrated, substantial changes are not found in the signal value. In an actual chart including shadows, however, the signal value is to change substantially.

The calculation function 153 performs the processing by the above-described threshold for each depth. That is, the calculation function 153 extracts a shadow portion in the ultrasonic image for each depth. In an ultrasonic image, because the intensity of the signal value for each depth differs by the gain, focus, and deep attenuation of the image, the threshold is to be defined for each depth when the signal value is used as it is. Consequently, in order to remove the gain, focus, and deep attenuation, the calculation function 153 can perform preprocessing to normalise the signal value before performing the above-described processing by the threshold.

Figure 4:
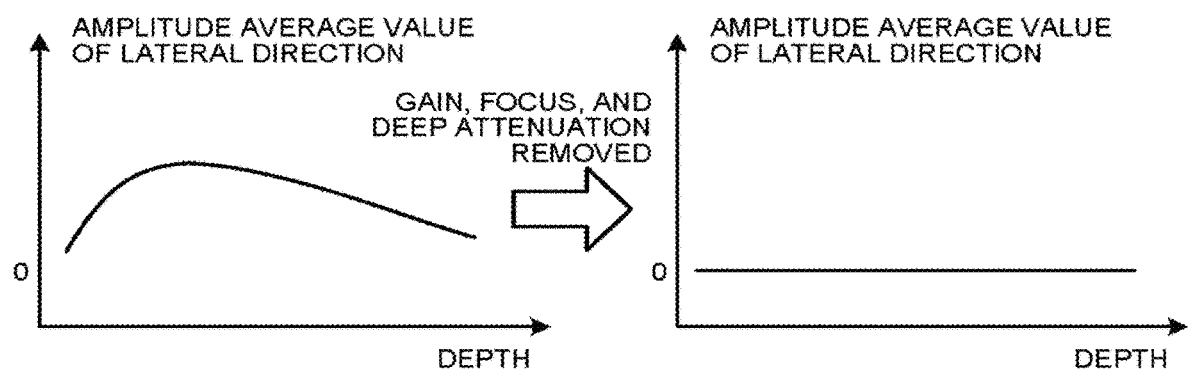
FIG. 4 is a diagram for explaining one example of preprocessing in the first embodiment.

FIG. 4 is a diagram for explaining one example of the preprocessing in the first embodiment. In FIG. 4, graphic charts with the ordinate axis representing an average value of the signals of the lateral direction and the abscissa axis representing the depth are illustrated. That is, in FIG. 4, graphic charts in which the average value of the signal values extracted in the orientation direction for each depth is calculated and graphed are illustrated. As illustrated in a left portion in FIG. 4, on the average value of the signal values for each depth, the average value of the signal values is high at a focused depth and the average value becomes lower as the depth becomes deeper, for example. Thus, when such signal values are used as they are, an appropriate threshold is to be defined for each depth.

Consequently, the calculation function 153, at least as a part of the analysis performed for each depth, calculates the average value of the signal values of a plurality of signals at an identical depth obtained by the ultrasound scan and calculates the difference between the average value and the signal value of the respective signals for each depth, and thereby generates the shadow information. In other words, the calculation function 153 generates the shadow information by calculating the respective average values of the signals for each depth, and by using the value obtained by subtracting the average value of the corresponding depth from the value of the signal for each depth. Explaining one example by using FIG. 3A, the calculation function 153 calculates the average value of the signal values "s1" to "s250" at the depth of "d1" and calculates respective values obtained by subtracting the calculated average value from the signal values "s1" to "s250." The calculation function 153 performs the above-described processing at all depths. That is, the calculation function 153, at all of the depths, calculates the respective values obtained by subtracting the average value of the corresponding depth from the signal value for each depth. Consequently, the values of the signals collected by the ultrasound scan are normalized, and as illustrated in a right portion in FIG. 4, the average value of the signals becomes "0," and thereby the processing can be performed by using a single threshold regardless of the depth.

Figure 5A:
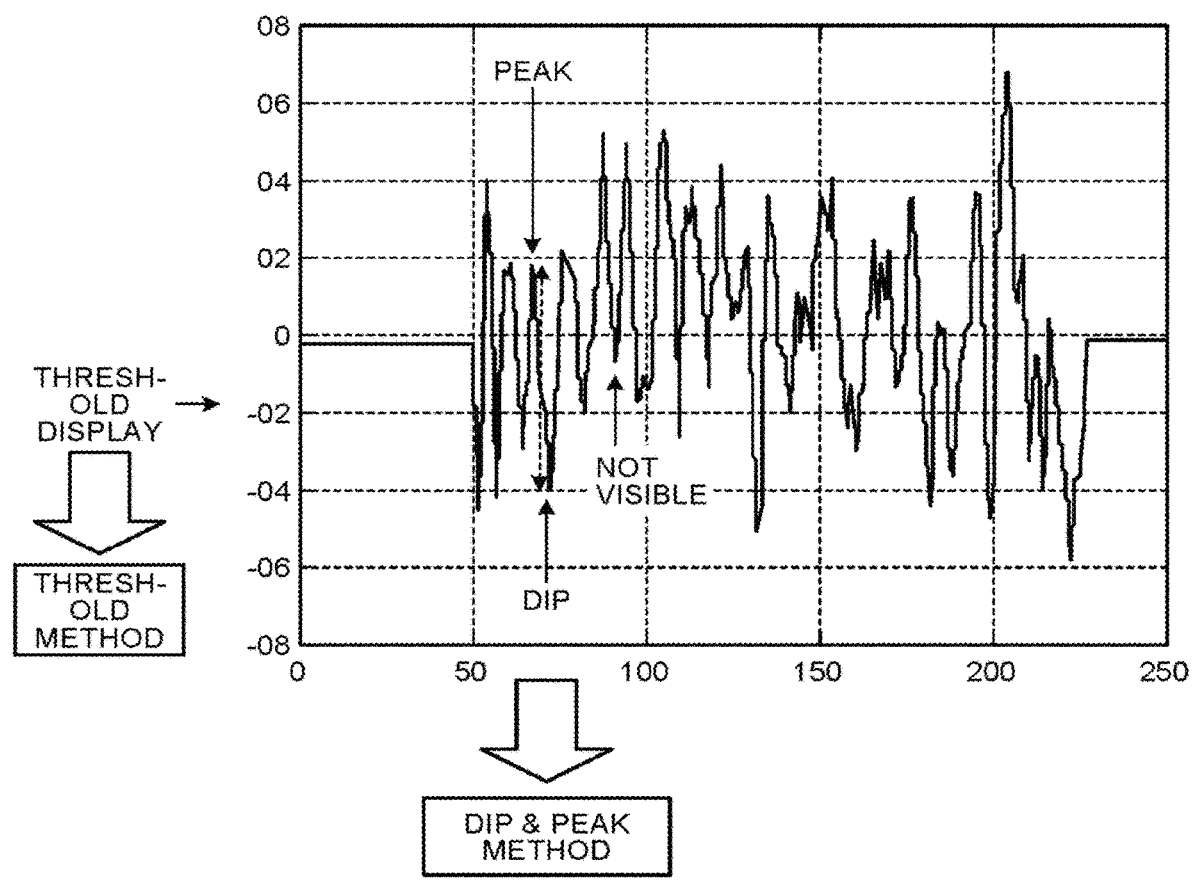
FIG. 5A is a diagram for explaining an example of threshold processing performed by the calculation function in the first embodiment.
Figure 5B:
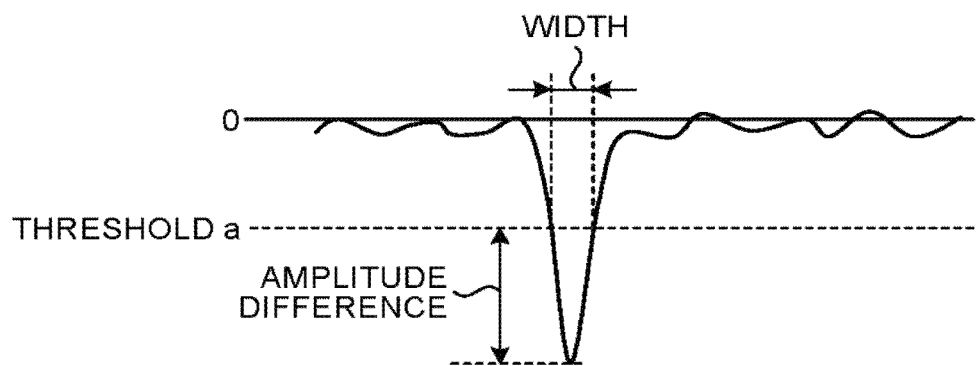
FIG. 5B is a diagram explaining an example of the threshold processing performed by the calculation function in the first embodiment.
Figure 5C:
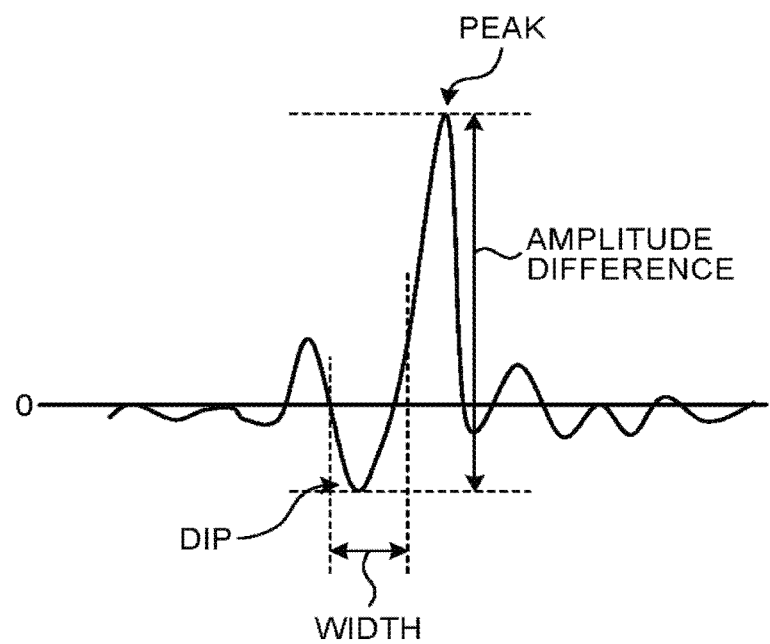
FIG. 5C is a diagram explaining an example of the threshold processing performed by the calculation function in the first embodiment.

Upon performing the preprocessing as in the foregoing, the calculation function 153 performs threshold processing by using the signal values after the preprocessing, and extracts shadow portions in the ultrasonic image. With reference to FIGS. 5A to 5C, the following describes an example of the threshold processing. FIGS. 5A to 5C are diagrams for explaining an example of the threshold processing performed by the calculation function 153 in the first embodiment. In FIG. 5A, illustrated is a graphic chart of the signal values after the preprocessing of pixels at an identical depth. FIGS. 5B and 5C illustrate a part of the chart.

For example, as Illustrated in FIG. 5A, the calculation function 153 performs "threshold method" that extracts a signal falling below a certain threshold in the signals for each depth, and "dip & peak method" that extracts a signal for which the difference between signals exceeds a certain threshold. In "threshold method," as illustrated in FIG. 5A, a threshold is defined for the signal value after the preprocessing, and the signal for which the signal value after the preprocessing falls below the threshold is extracted as a shadow, for example. That is, the calculation function 153 extracts as a shadow portion, in the pixels at an identical depth, the pixels for which the signal value after the preprocessing falls below the threshold.

For example, as illustrated in FIG. 5B, the calculation function 153 extracts as a shadow, in the chart of the signal value after the preprocessing, the pixels (sample points) corresponding to the portion for which the signal value falls below a threshold a. The calculation function 153, as illustrated in FIG. 5B, calculates "amplitude difference" that is the difference between the threshold and "dip" of the signal value and "width" of the portion extracted as the shadow, as the features of a shadow.

In "dip & peak method," as illustrated in FIG. 5A, the signal of the portion for which the difference between "peak" and "dip" in the chart exceeds a certain threshold is extracted as a shadow, for example. That is, the calculation function 153 extracts de a shadow portion, in the pixels at an identical depth, the pixels of the portion for which the degree of peak and dip in the signal value after the preprocessing is large. In the portions in which the shadow arises, the baseline is not always low, and there may be a case in which extraction cannot be performed with a simple threshold. For example, at the position indicated as "not visible" in FIG. 5A, although the portion of "dip" of the signal value is of a value higher than the threshold in "threshold method," a shadow has arisen in practice in that portion. The "dip & peak method" can extract shadows in such a portion. As for "peak" and "dip" in the chart, signals may be adjacent and the signals may not be adjacent. That is, there may be a case in which two adjacent signals are "peak" and "dip" and there may be a case in which two signals not being adjacent are "peak" and "dip" (a case in which another signal is included between the signals corresponding to "peak" and "dip"). The calculation function 153 compares a certain threshold with the difference in the respective signal values corresponding to "peak" and "dip" of the pixels (signals) at an identical depth, and thereby extracts shadows.

For example, as illustrated in FIG. 5C, the calculation function 153 calculates "amplitude difference" that is the difference between "peak" and "dip" and extracts, as a shadow, the portion in which the calculated "amplitude difference" exceeds the certain threshold. The calculation function 153, as illustrated in FIG. 5C, calculates respective positions at which the signal value becomes a half value of "amplitude difference" between "dip" extracted as a shadow and "peak" on both sides, extracts as the shadow the pixels (sample points) corresponding to a portion between the positions at which the value becomes the calculated half values, and then calculates "width" of the portion extracted as the shadow, for example.

As in the foregoing, the calculation function 153 extracts portions of shadows for each depth by using "threshold method" or "dip & peak method" and calculates "amplitude difference" and "width" of the shadows as the features of the extracted shadows. It may be a case of extracting the shadows by either one of the above-described "threshold method" and "dip & peak method," but may be a case of extracting the shadows by using both "threshold method" and "dip & peak method." In such a case, the calculation function 153, out of the portions extracted as shadows by "dip & peak method," extracts as the shadows the portion that falls below the threshold of "threshold method" in the signal value, for example. The above-described extraction processing of shadows may be a case intended for a whole of the ultrasonic image, but may be a case intended for a certain region. In such a case, the input unit receives the setting of an ROI, and the processing circuitry 15 extracts shadows within the received ROI, for example.

Figure 6:
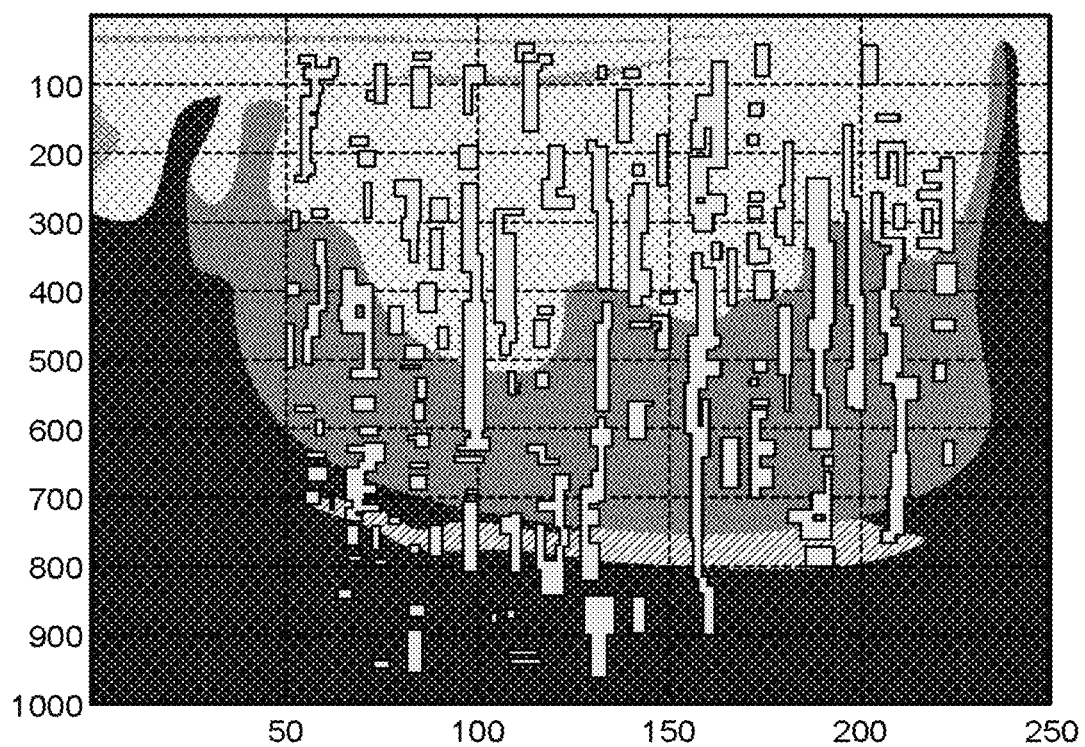
FIG. 6 is a diagram illustrating one example of a superimposed image in the first embodiment.

The ultrasonic diagnostic apparatus in the first embodiment can provide a variety of information by using the information on extracted shadows. The image generation function 151 generates, based on the shadow information, a shadow image indicating at least one of the positions and features of the shadows, for example. In one example, the image generation function 151 generates a superimposed image in which the shadow image is superimposed on a morphologic image based on the result of the ultrasound scan. FIG. 6 is a diagram illustrating one example of a superimposed image in the first embodiment. In FIG. 6, illustrated is a superimposed image in which a shadow image indicating the positions of shadows is superimposed on a B-mode image before scan conversion, with the depth in the longitudinal direction and the scanning lines in the lateral direction.

For example, when the areas (positions) of shadows in an ultrasonic image are extracted by calculation function 153, the image generation function 151 generates a superimposed image in which, as illustrated in FIG. 6, the positions of the shadows are indicated on a B-mode image. This enables an observer to perceive the positions of the shadows in the ultrasonic image at a glance.

Figure 7:
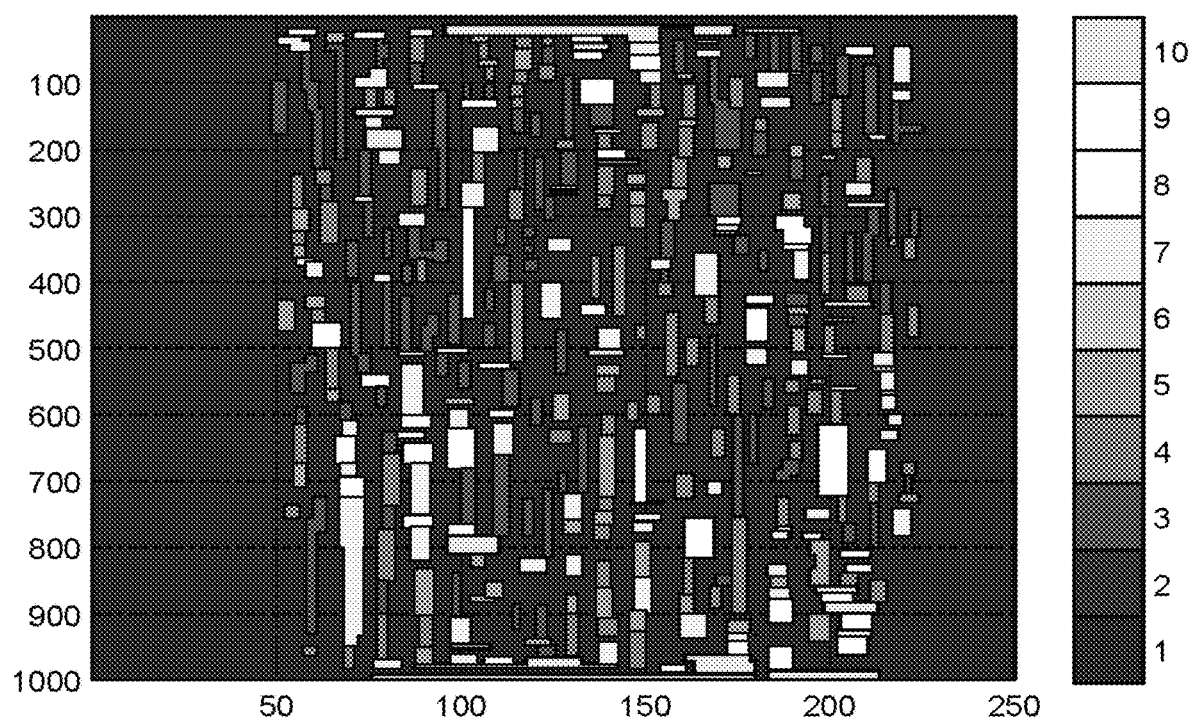
FIG. 7 is a diagram illustrating one example of a shadow image in the first embodiment.

The image generation function 151 can also generate a shadow image by assigning at least one of the hue, saturation, and lightness depending on the features of the shadows. FIG. 7 is a diagram illustrating one example of a shadow image in the first embodiment. In FIG. 7, illustrated is a shadow image using "width" as the feature of a shadow. For example, as illustrated in FIG. 7, the image generation function 151 assigns a color for the shadows of "width: 1 to 10" and generates a shadow image colorized depending on "width" of the shadows. In FIG. 7, the case of using "width" as the feature of a shadow has been exemplified. However, the embodiment is not limited to this, and it may be a case of using "amplitude difference" and a case of using both "width" and "amplitude difference."

Figure 8:
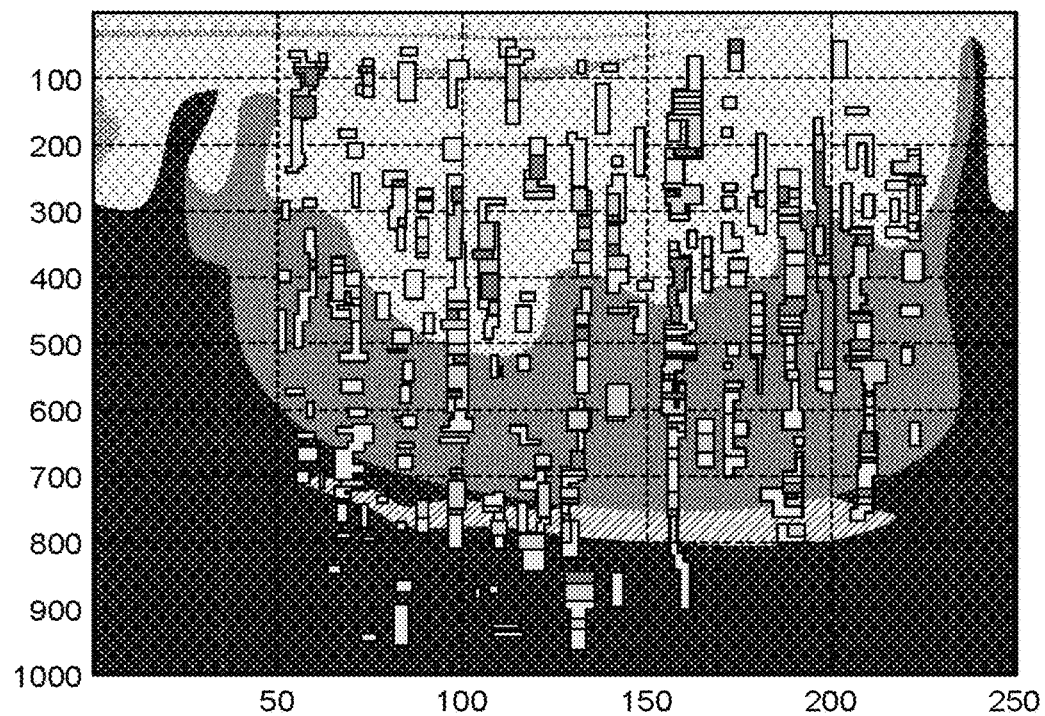
FIG. 8 is a diagram illustrating one example of a superimposed image in the first embodiment.

The image generation function 151 can also generate superimposed image in which a shadow image indicating the features of shadows is superimposed on a morphologic image. FIG. 8 is a diagram illustrating one example of a superimposed image in the first embodiment. FIG. 8 illustrates a superimposed image in which a shadow image using "amplitude difference" as the feature of a shadow is superimposed on a B-mode image before scan conversion. For example, as illustrated in FIG. 8, the image generation function 151 assigns colors for each degree of amplitude difference and generates a shadow image colorized in accordance with "amplitude difference" of the extracted shadows. For example, the image generation function 151 assigns colors in three stages depending on the degree of "amplitude difference" and colorizes shadows in accordance with "amplitude difference" of the shadows.

The image generation function 151 then, as illustrated in FIG. 8, generates the superimposed image in which the generated shadow image is superimposed on the B-mode image. In FIG. 8, the case of using "amplitude difference" as the feature of a shadow has been exemplified. However, the embodiment is not limited to this, and it may be a case of using "width" and a case of using both "width" and "amplitude difference."

When the superimposed images and the shadow images illustrated in FIGS. 6 to 8 are generated, the control function 152 performs control such that the display 2 displays thereon the generated superimposed image and the shadow image. The observer can, by observing these images, perceive at a glance the positions of the shadows, and the features of the shadows at each position in the ultrasonic image.

In the above-described example, the case of displaying a shadow image has been described. The ultrasonic diagnostic apparatus in the first embodiment, however, can also perform various measurements concerning shadows. Specifically, the calculation function 153 performs measurement concerning shadows based on the shadow information. For example, the calculation function 153 measures at least one of the value indicating the feature of a shadow and the rate of the shadow occupying the result of an ultrasound scan.

Figure 9:
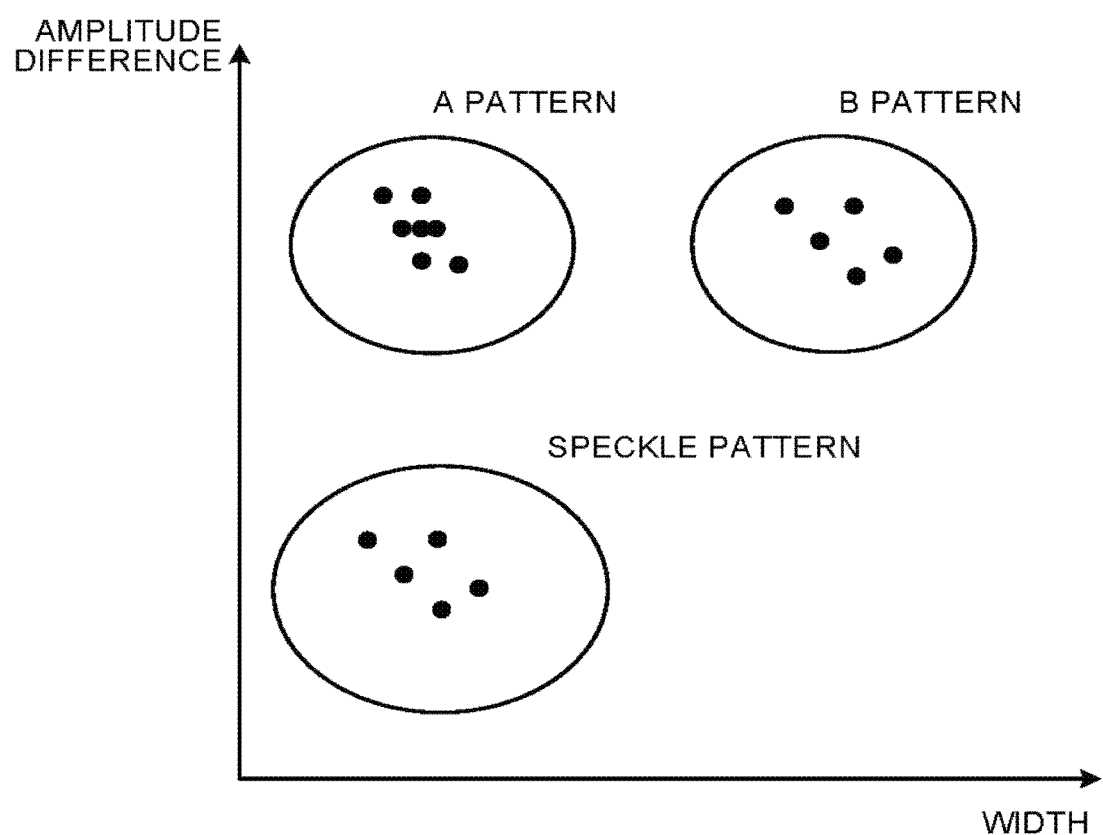
FIG. 9 is a diagram for explaining one example of patterns of shadows in the first embodiment.

As in the foregoing, the calculation function 153 calculates "amplitude difference" and "width" as the features of a shadow. The calculation function 153 can further determine, based on the calculated "amplitude difference" and "width," patterns of the shadows. FIG. 9 is a diagram for explaining one example of patterns of the shadows in the first embodiment. In FIG. 9, illustrated is a scatter diagram (conceptual diagram) with the ordinate axis representing "amplitude difference" and the abscissa axis representing "width."

For example, the calculation function 153 extracts shadow portions by at least one of the above-described "threshold method" and "dip & peak method" and calculates "amplitude difference" and "width." The calculation function 153 then, as illustrated in FIG. 9, classifies, based on "amplitude difference" and "width," the extracted shadows into shadows of "A pattern," shadows of "B pattern," and "speckle pattern."

In one example, the calculation function 153 classifies, out of ones extracted as shadows, the one that indicates low values in both "amplitude difference" and "width" as "speckle pattern." The calculation function 153 classifies as shadows of "A pattern," out of the ones extracted as shadows, the one that indicates a high value in "amplitude difference" and indicates a low value in "width." The calculation function 153 classifies, out of the ones extracted as shadows, the one that indicates high values in both "amplitude difference" and "width" as shadows of "B pattern."

As in the foregoing, the calculation function 153 classifies the extracted shadows into various patterns based on the features of the shadows. Consequently, the ones extracted as shadows can be further classified into the shadows and speckles, for example. Furthermore, the shadows of narrow "width" such as pectinate shadows and the shadows of wide "width" arising from bones or others can be classified as "A pattern" and "B pattern," respectively, for example. The values of "amplitude difference" and "width" for classifying the respective patterns can be defined arbitrarily. That is, the shadows can be classified based on the values indicating the features of the shadows, and the shadows can be quantitatively analyzed.

Figure 10:
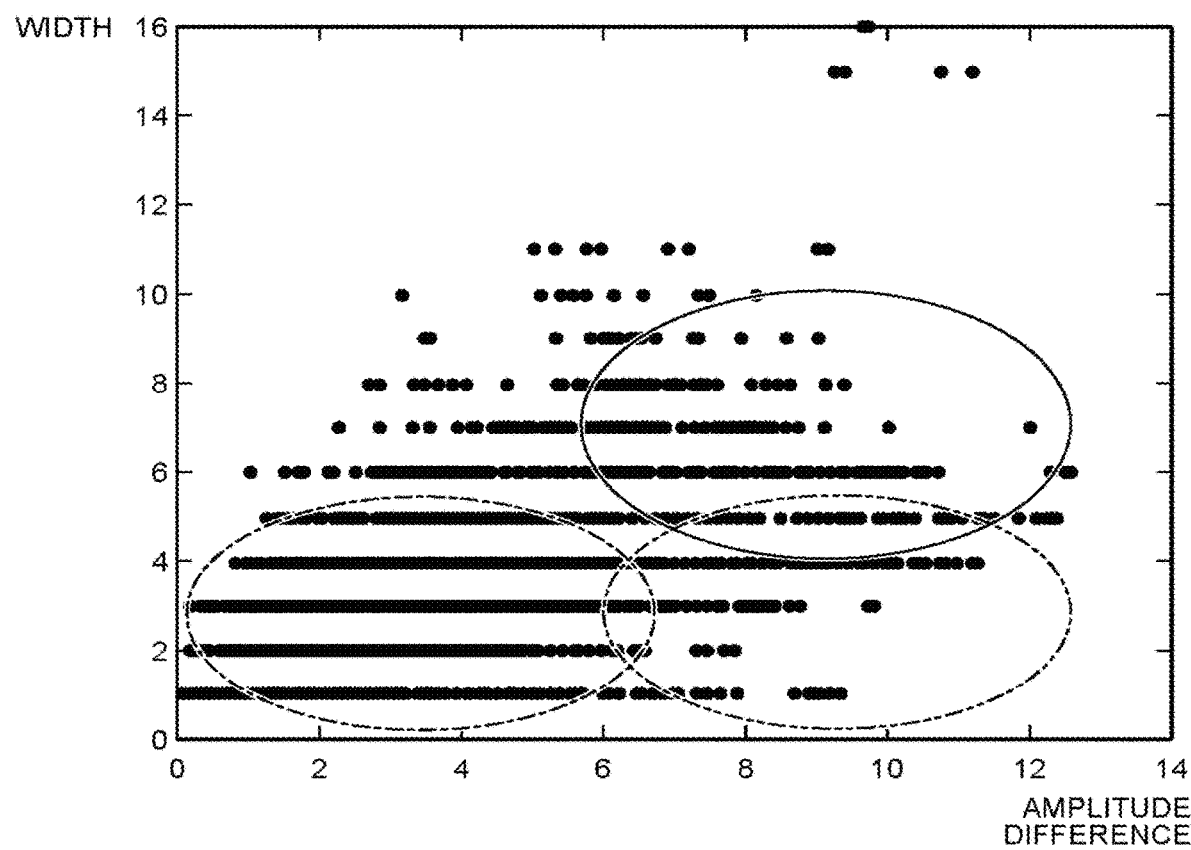
FIG. 10 is a diagram for explaining one example of a pattern classification of shadows in the first embodiment.

FIG. 10 is a diagram for explaining one example of a pattern classification of shadows in the first embodiment. In FIG. 10, illustrated is a scatter diagram with the ordinate axis representing "width (the number of pixels)" and the abscissa axis representing "amplitude difference." For example, as illustrated in FIG. 10, the calculation function 153 classifies the shadows into the respective patterns by defining in the scatter diagram three areas of an area corresponding to "A pattern," an area corresponding to "B pattern," and an area corresponding to "speckle pattern." The ones included in a portion in which the areas are overlapped in FIG. 10 may be classified into either of the patterns depending on the distance from the boundary of the area, or may be classified into neither of the patterns.

Figure 11:
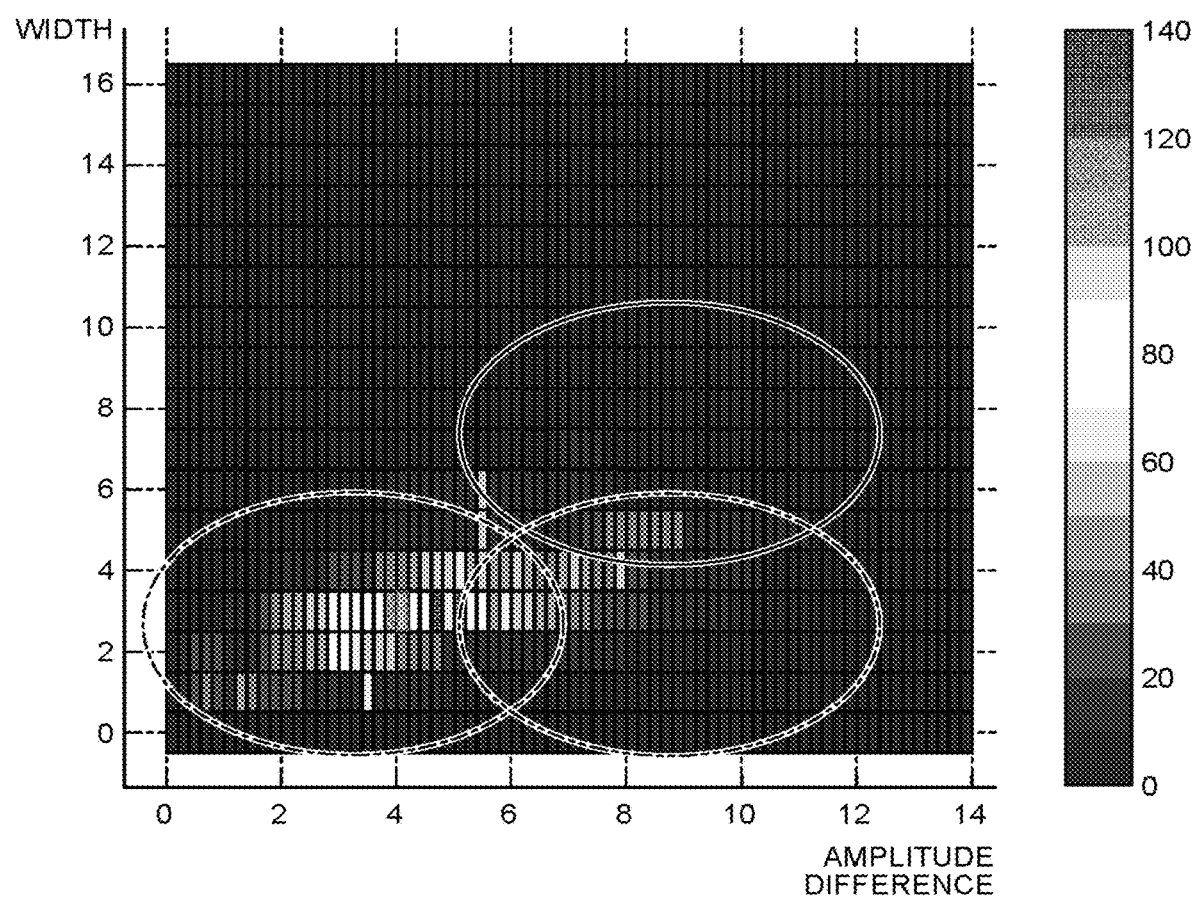
FIG. 11 is a diagram illustrating one example of a color map of the features of shadows in the first embodiment.

FIG. 11 is a diagram illustrating one example of a color map of the features of shadows in the first embodiment. In FIG. 11, Illustrated is a color map in which colors are assigned to the difference in frequency of occurrence, with the ordinate axis representing "width (the number of pixels)" and the abscissa axis representing "amplitude difference." For example, the calculation function 155 counts the umber of occurrences for each value of "amplitude difference" and each value of "width," extracts the colors corresponding to the counted values from a color bar, and performs colorization. As illustrated in FIG. 11, the classification of patterns may be performed based on the color map.

When the pieces of information illustrated in FIGS. 9 to 11 are generated, the control function 152 performs control such that the display 2 displays thereon the generated pieces of information. The observer can, by observing these pieces of information, perceive at a glance the patterns of the extracted shadows and the difference in frequency of occurrence thereof. In FIGS. 9 to 11, the cases of classifying the extracted shadows into three patterns have been exemplified. The embodiment, however, is not limited to this, and may be a case of classifying the extracted shadows into the patterns of two, or four or more, for example.

As in the foregoing, the calculation function 153 can measure a variety of information concerning the shadows. The image generation function 151 can generate various images by using the information measured by the calculation function 153. For example, the image generation function 151 generates a shadow image in which at least one of the hue, saturation, and lightness is assigned depending on the patterns of the shadows, and generates a superimposed image in which the generated shadow image is superimposed on a morphologic image based on the result of the ultrasound scan.

Figure 12:
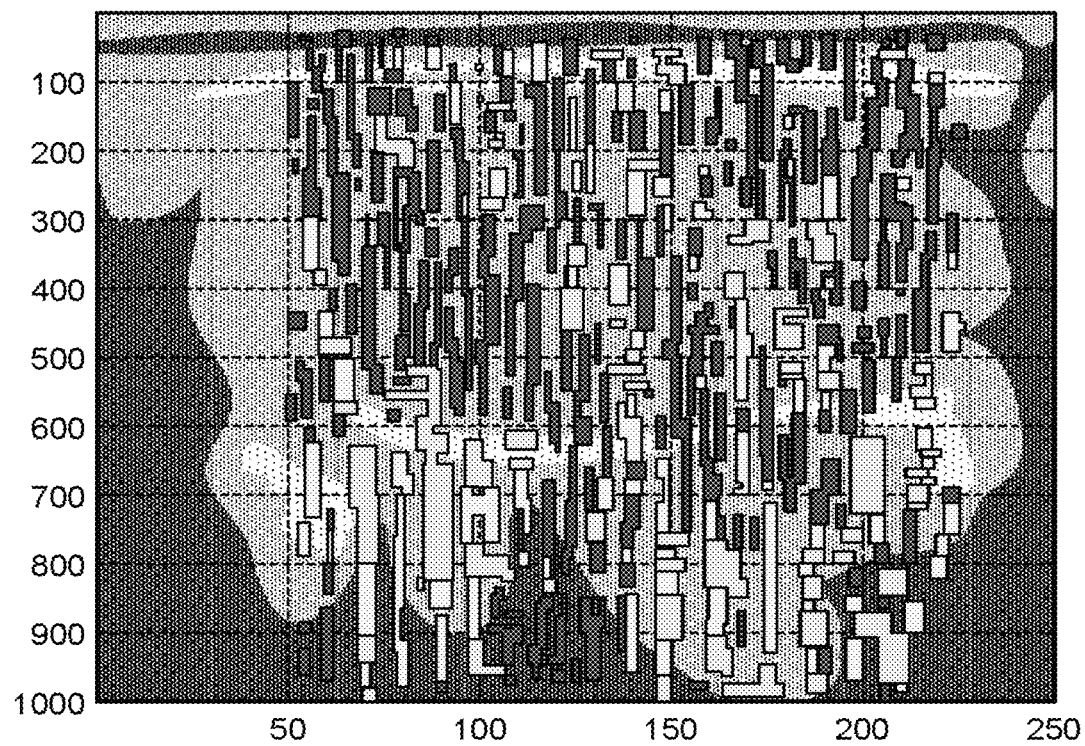
FIG. 12 is a diagram illustrating one example of a superimposed image in the first embodiment.

FIG. 12 is a diagram illustrating one example of a superimposed image in the first embodiment. FIG. 12 illustrates a superimposed image in which a shadow image in which colors have been assigned to the three patterns described with reference to FIGS. 9 to 11 is superimposed on a B-mode image before scan conversion. For example, as illustrated in FIG. 12, the image generation function 151 assigns colors to "speckle pattern," "A pattern," and "B pattern" and generates a shadow image colorized in accordance with the patterns of the extracted shadows.

The image generation function 151 then, as illustrated in FIG. 12, generates a superimposed image in which the generated shadow image is superimposed on the B-mode image. The control function 152 causes the display 2 to display thereon the generated superimposed image. Consequently, the patterns of the shadows on the image can be perceived at a glance. In FIG. 12, the case of classifying the shadows into three patterns has been exemplified. The embodiment, however, is not limited to this, and may be a case in which the shadows are classified into the patterns of two, or four or more, for example. In such a case, colors are assigned such that respective patterns are distinguishable, and then a shadow image is generated.

Figure 13A:
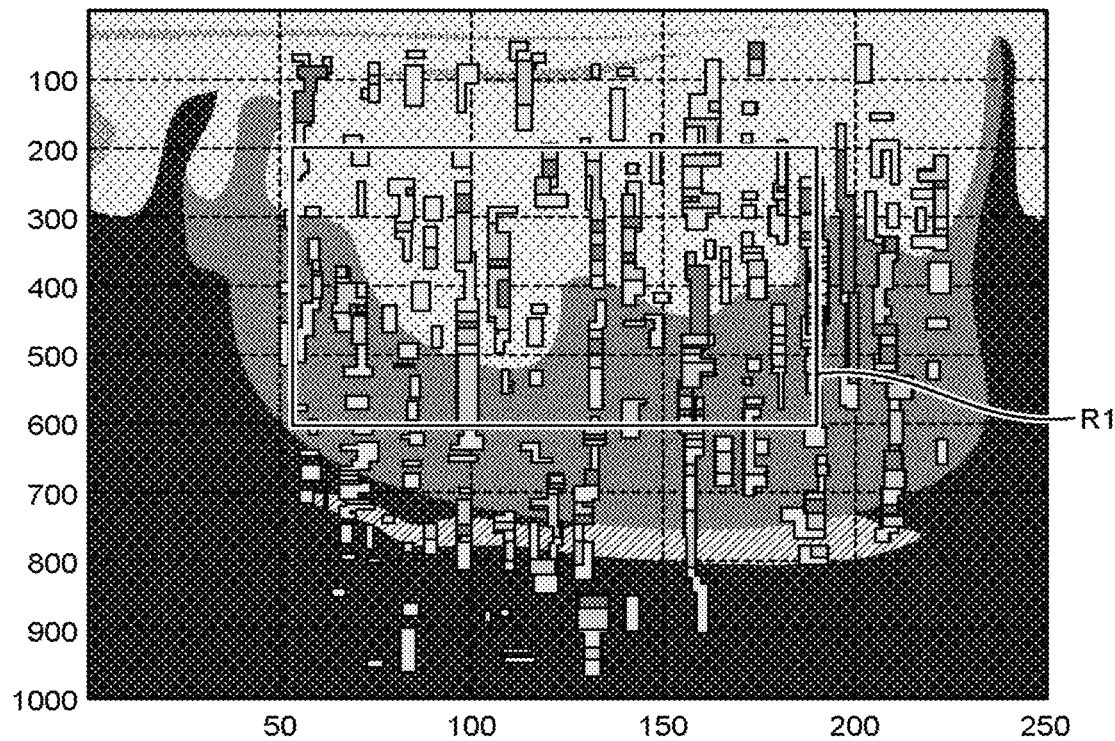
FIG. 13A is a diagram for explaining one example of calculating rates of shadows in the first embodiment.
Figure 13B:
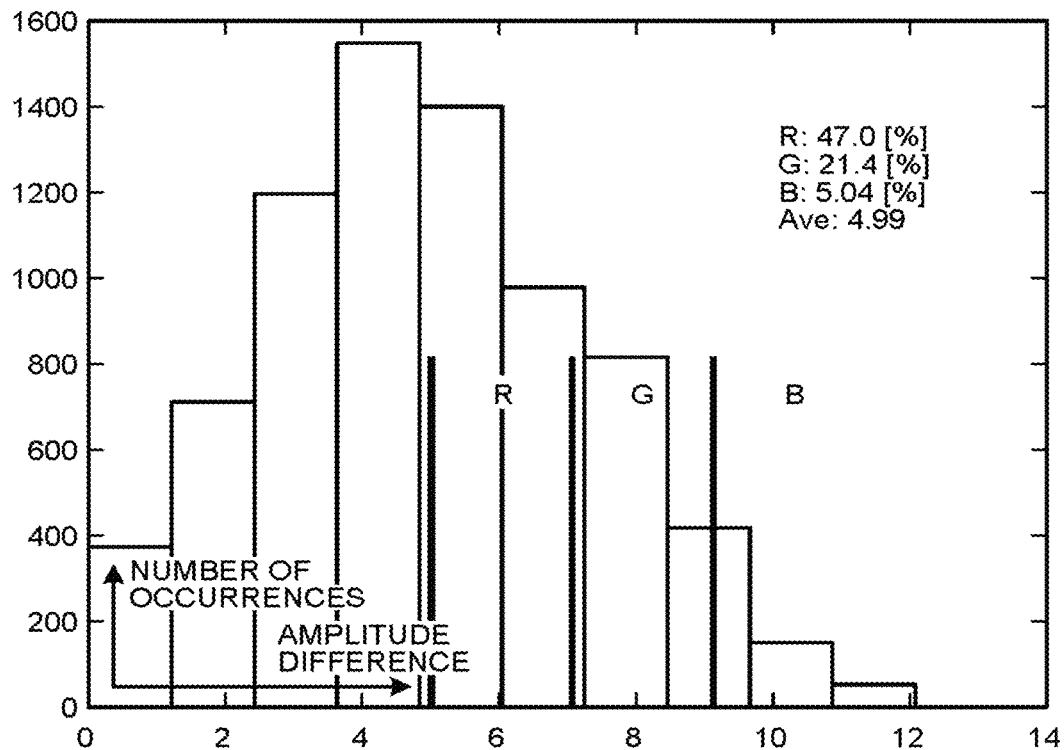
FIG. 13B is a diagram for explaining one example of calculating the rates of shadows in the first embodiment.

As in the foregoing, the image generation function 151 can generate various images by using the information calculated by the calculation function 153. The calculation function 153 can measure a variety of information in addition to the above-described examples. For example, the calculation function 153 can calculate the rate of shadows in an ultrasonic image. FIGS. 13A and 13B are diagrams for explaining one example of calculating the rates of shadows in the first embodiment. In FIG. 13A, illustrated is a diagram in which an area "R1" is defined on the superimposed image (a superimposed image in which shadows are colorized in accordance with the difference in the amplitude difference) illustrated in FIG. 8. FIG. 13B illustrates frequency distribution with the ordinate axis representing the number of occurrences and the abscissa axis representing "amplitude difference."

For example, as illustrated in FIG. 13A, when the input unit 3 receives a setting operation of the area "R1," the calculation function 153 calculates the rates of the shadows in the area "R1" defined. For example, the calculation function 153 calculates each "amplitude difference" on all of the pixels included in the area "R1" and generates the frequency distribution illustrated in FIG. 13B by using calculated "amplitude difference." The calculation function 153 then calculates the rates of the pixels extracted as shadows. For example, the calculation function 153 calculates each of the rates of the shadows divided into three stages by the degree of "amplitude difference."

In one example, as illustrated in FIG. 13B, the calculation function 153 calculates the rate "47.0%" of the shadows that are of "amplitude difference: 5 to 7" and indicated in "red" on the superimposed image. The calculation function 153 calculates the rate "21.4%" of the shadows that are of "amplitude difference: 7 to 9" and indicated in "green (G)" on the superimposed image, as illustrated in FIG. 13B. The calculation function 153 further calculates the rate "5.04%" of the shadows that are of "amplitude difference: equal to or higher than 9" and indicated in "blue (B)" on the superimposed image.

The calculation function 153 can, as illustrated in FIG. 13B, further calculate the average "4.99" of "amplitude difference" in the area "R1." Although not illustrated, the calculation function 153 can calculate not only the average value but also a standard deviation and others. When the rates of the shadows are calculated by the calculation function 153 as in the foregoing, the control function 152 causes the display 2 to display thereon the calculation result. For example, the control function 152 causes the display 2 to display thereon the frequency distribution and the information on the rates illustrated in FIG. 13B.

The calculation function 153 can also calculate, as the above-described rate of shadows, the rate for each pattern of the shadows. For example, the calculation function 153 can also calculate the rates of "speckle pattern," "A pattern," and "B pattern" on the area "R1" and generate the frequency distribution.

Figure 14:
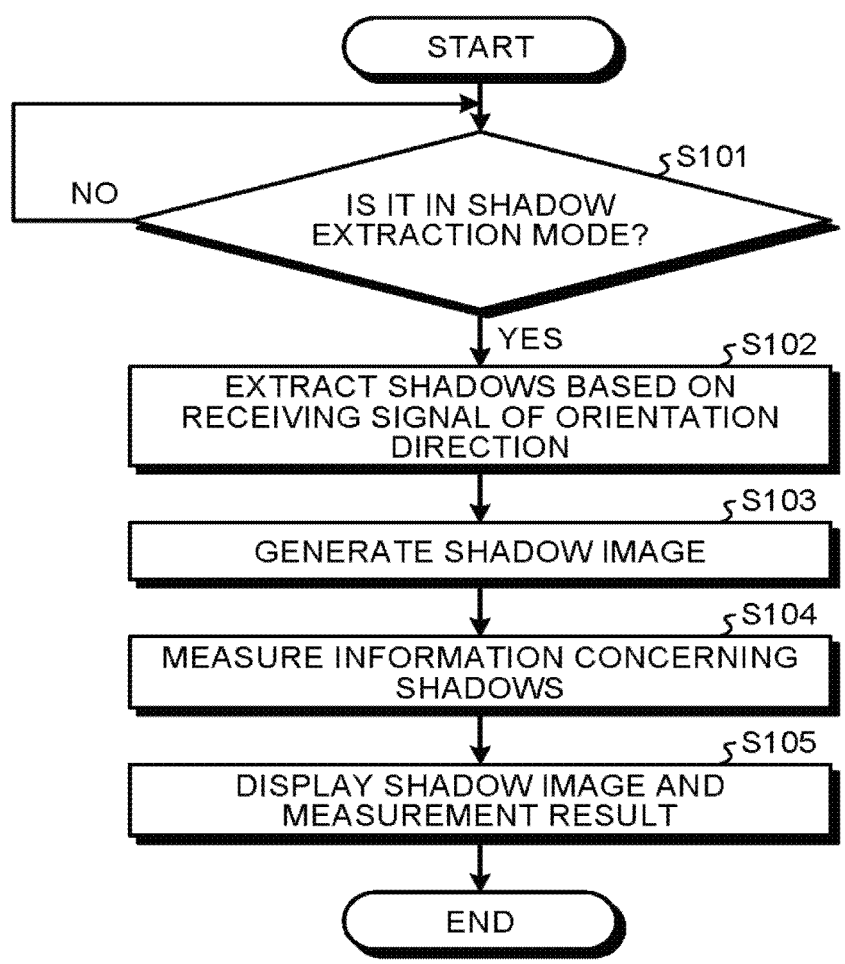
FIG. 14 is a flowchart for explaining an example of processing performed by the ultrasonic diagnostic apparatus in the first embodiment.

Next, with reference to FIG. 14, the processing performed by the ultrasonic diagnostic apparatus in the first embodiment will be described. FIG. 14 is a flowchart for explaining an example of the processing performed by the ultrasonic diagnostic apparatus in the first embodiment. In FIG. 14, the processing in which a shadow image and measurement result are displayed is illustrated. Step S101 illustrated in FIG. 14 is a step in which the processing circuitry 15 reads out the computer program corresponding to the control function 152 from the internal storage circuitry 16 and executes the read computer program. At Step S101, the processing circuitry 15 determines whether the mode has been changed to a shadow extraction mode. Step S102 is a step in which the processing circuitry 15 reads out the computer program corresponding to the calculation function 153 from the internal storage circuitry 16 and executes the read computer program. At Step S102, when the shadow extraction mode is determined (yes at Step S101), the processing circuitry 15 extracts shadows based on a receiving signal of the orientation direction.

Step S103 is a step in which the processing circuitry 15 reads out the computer program corresponding to the image generation function 151 from the internal storage circuitry 16 and executes the read computer program. At Step S103, the processing circuitry 15 generates a shadow image. Step S104 is a step in which the processing circuitry 15 reads out the computer program corresponding to the calculation function 153 from the internal storage circuitry 16 and executes the read computer program. At Step S104, the processing circuitry 15 measures information concerning the shadows.

Step S105 is a step in which the processing circuitry 15 reads out the computer program corresponding to the control function 152 from the internal storage circuitry 16 and executes the read computer program. At Step S105, the processing circuitry 15 causes the display 2 to display thereon the shadow image and the measurement result. In the above-described example of the processing, the case in which the information concerning the shadows is measured after having generated the shadow image has been exemplified. The embodiment, however, is not limited to this, and it may be a case in which a shadow image is generated after having measured the information concerning shadows, or may be a case in which the generation of a shadow image and the measurement are performed at the same time.

As in the foregoing, according to the first embodiment, the control function 152 causes the ultrasonic probe to perform an ultrasound scan of the subject. The calculation function 153 analyzes the result f the ultrasound scan for each depth, and generates shadow information that is information concerning the shadows that have appeared in the result of the ultrasound scan based on the result of the analysis on a plurality of depths. Consequently, the ultrasonic diagnostic apparatus in the first embodiment makes it possible to perform the extraction of shadows in an ultrasound image accurately.

For example, in conventional technologies, a technology that extracts, by analyzing an ultrasonic image in a depth direction, shadows in the image has been known. However, in such a conventional technology, after having extracted a hard tissue, a tissue on the underside of the hard tissue is extracted as shadows, and the whole tissue underneath the hard tissue is extracted as the shadows. For example, the shadows that arise at the time a liver is scanned appear not only from within the liver but also from the liver surface (including the vicinity thereof) and the vicinity of an abdominal wall. Consequently, processing in a distance direction as in the conventional technology can be greatly affected by the structure from the abdominal surface to the liver surface. For example, when there is a hard tissue on the abdominal surface, the positions deeper than that tissue are all extracted as shadows.

However, in the ultrasonic diagnostic apparatus in first embodiment, because the processing is performed the orientation direction, it is also possible to distinguish whether the shadows are from the abdominal surface, the liver surface, or within the liver. Moreover, in the ultrasonic diagnostic apparatus in the first embodiment, even when the shadows arise in a phased manner in the depth direction, the respective shadows can be extracted, for example.

Furthermore, according to the first embodiment, the image generation function 151 generates, based on the shadow information, a shadow image that represents at least one of the positions and features of the shadows. The image generation function 151 generates a shadow image by assigning at least one of the hue, saturation, and lightness depending on the features of the shadows. The image generation function 151 further generates a superimposed image in which the shadow image is superimposed on a B-mode image based on the result of the ultrasound scan. Consequently, the ultrasonic diagnostic apparatus in the first embodiment makes it possible to provide an image that is easy to observe shadows in an ultrasound image.

According to the first embodiment, the calculation function 153 determines the pattern of shadows based on the features of the shadows, and the image generation function 151 generates a shadow image by assigning at least one of the hue, saturation, and lightness depending on the pattern of the shadows, and generates a superimposed image in which the generated shadow image is superimposed on a B-mode image based on the result of the ultrasound scan. Consequently, the ultrasonic diagnostic apparatus in the first embodiment makes it possible to provide information in which the features of the shadows are reflected.

According to the first embodiment, the calculation function 153 performs measurement concerning the shadows based on the shadow information. The calculation function 153 further measures at least one of the value indicating the feature of a shadow, and the rate of the shadow occupying the result of the ultrasound scan. Consequently, the ultrasonic diagnostic apparatus in the first embodiment makes it possible to analyze the shadows quantitatively.

According to the first embodiment, the calculation function 153, at least as a part of the analysis performed for each depth, performs at least one of the comparison between a certain threshold and a signal value of each signal at an identical depth obtained by the ultrasound scan and the comparison between a certain threshold and a difference between the signal value of each signal obtained at an identical depth obtained by the ultrasound scan and a reference value, and thereby generates the shadow information. Consequently, the ultrasonic diagnostic apparatus in the first embodiment makes it possible to perform the extraction of shadows in the orientation direction easily. Moreover, the ultrasonic diagnostic apparatus in the first embodiment can also extract the shadows that are difficult to extract in "threshold method."

According to the first embodiment, the calculation function 153, at least as a part of the analysis performed for each depth, calculates an average value of signal values of a plurality of signals at an identical depth obtained by the ultrasound scan and calculates the difference between the average value and the signal value of the respective signals for each depth, and thereby generates the shadow information. Consequently, the ultrasonic diagnostic apparatus in the first embodiment makes it possible to normalize the signal values and facilitate the processing.

Second Embodiment

While the first embodiment has been explained in the foregoing, the embodiment may be implemented in various different forms in addition to the above-described first embodiment.

Figure 15A:
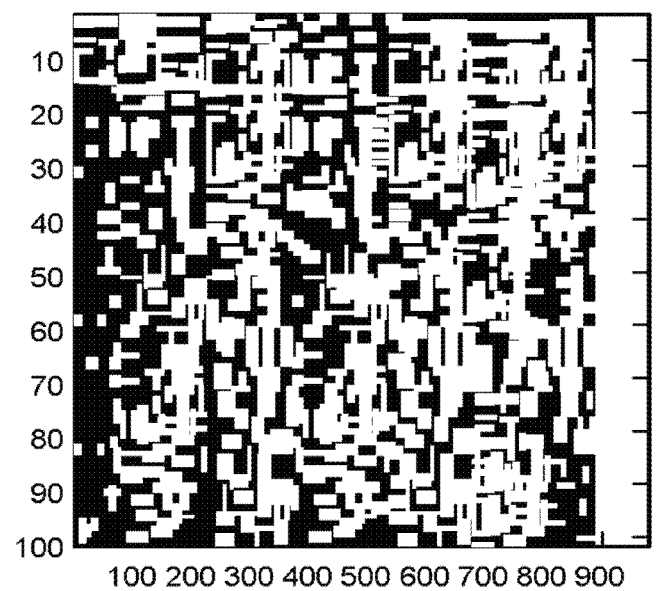
FIG. 15A is a diagram schematically illustrating one example of preprocessing according to a second embodiment.
Figure 15B:
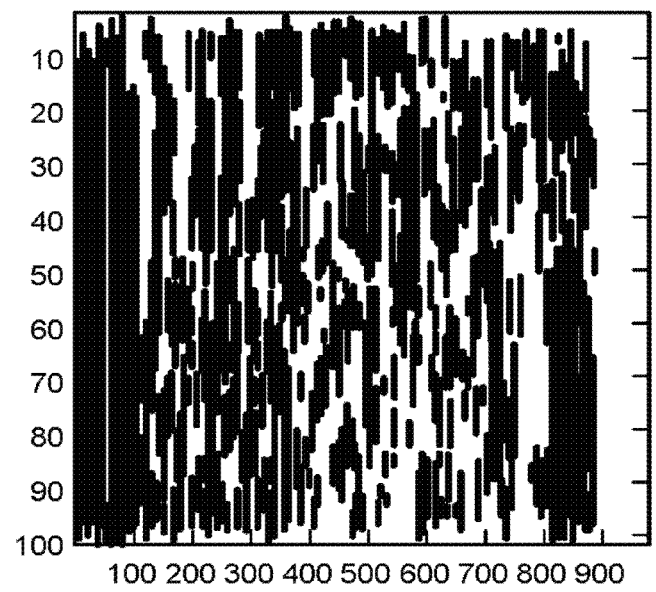
FIG. 15B is a diagram schematically illustrating one example of the preprocessing in the second embodiment.

In the above-described first embodiment, the situation of performing the subtraction processing of the average value as the preprocessing has been explained. The embodiment, however, is not limited to this, and other processing can also be performed as the preprocessing. For example, the preprocessing that removes speckle patterns included in the ultrasonic image can also be performed. Specifically, the calculation function 153 generates the shadow information after having applied a smoothing filter in the depth direction to the signals collected by the ultrasound scan. FIGS. 15A and 15B are diagrams schematically illustrating one example of the preprocessing according to a second embodiment.

For example, the calculation function 153, by applying a smoothing filter in the depth direction to the ultrasonic image illustrated in FIG. 15A, obtains the ultrasonic image illustrated in FIG. 15B. Consequently, as illustrated in FIG. 15B, speckle components are reduced, whereby the extraction of shadows can be performed more accurately.

In the above-described first embodiment, the situation in which the amplitude data or the luminance value is used as the result of the ultrasound scan has been exemplified. The embodiment, however, is not limited to this, and the reflected wave data including phase information before the envelop detection processing can also be used. In such a case, the calculation function 153 extracts shadows by a method different from the above-described "threshold method." For example, when performing analysis on the signals including phase information, the calculation function 153, at least as a part of the analysis performed for each depth, performs the comparison between the amplitude of the signal including the phase information and a plurality of thresholds, and thereby generates the shadow information.

In one example, when the signals collected by the ultrasound scan include the phase information, the calculation function 153 extracts the signals for which the amplitude is included within a certain range in the signals for each depth, and generates the shadow information.

Figure 16:
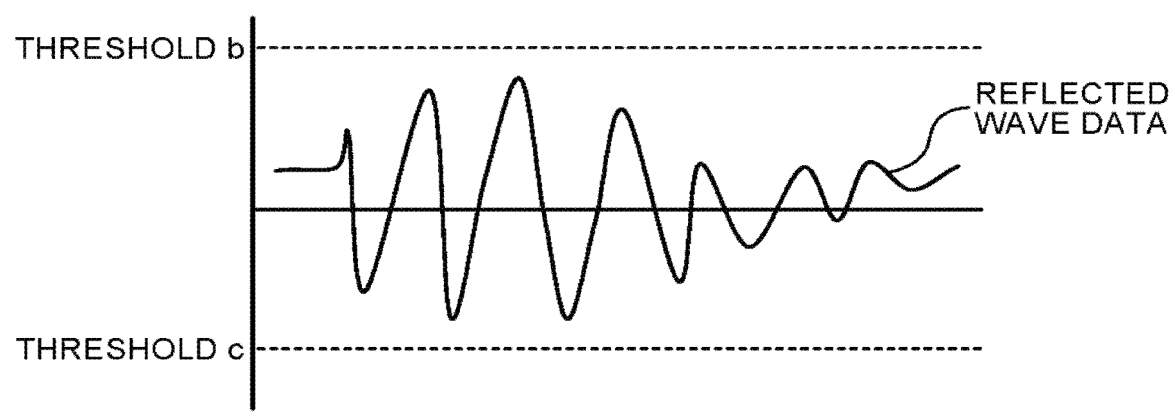
FIG. 16 is a diagram for explaining one example of threshold setting in the second embodiment.

FIG. 16 is a diagram explaining one example of threshold setting in the second embodiment. For example, as illustrated in FIG. 16, the calculation function 153 extracts shadows by using an upper side threshold b and a lower side threshold c that are defined for the reflected wave data. In one example, as illustrated in FIG. 16, when the reflected wave data is within the range of the threshold b and the threshold c, the calculation function 153 extracts the position of that reflected wave data as a shadow. Meanwhile, when the reflected wave data exceeds either one of the threshold b and the threshold c, the calculation function 153 determines that the data is not a shadow. The threshold b and the threshold c can be defined arbitrarily.

When the reflected wave data including phase information is used, it may be a case of extracting shadows by making the reflected wave data into amplitude information by squaring the reflected wave data, and using the above-described "threshold method" and "dip & peak method."

In the above-described first embodiment, the situation of using "amplitude difference" and "width" as the features of a shadow has been exemplified. The embodiment, however, is not limited to this, and it may be a case of using the information on the depth that is the origin of shadow and the analysis result of frequency analysis on the reflected wave data of the signal that has been extracted as a shadow, for example.

In the above-described first embodiment, the situation of performing the traction processing of the average value as the preprocessing has been explained. The embodiment, however, is not limited to this, and it may be a situation of not performing the subtraction processing of the average value. In such a case, the threshold in "threshold method" and the threshold in "dip & peak method" are defined for each depth. The calculation function 153 then extracts shadows by using "threshold method" and "dip & peak method" using the corresponding thresholds for each depth.

In the above-described first embodiment, the situation of calculating the rates of "patterns" classified based on "amplitude difference" and the shadow information and displaying the calculation result on the display 2 has been explained. The embodiment, however, is not limited to this, and it is also possible to further display a variety of information based on the calculation result. Specifically, the calculation function 153 measures the rate of shadows occupying the result of the ultrasound scan. The control function 152 then provides information about a relevant disease based on the rate of shadows measured by the calculation function 153. In one example, as illustrated in FIG. 13B, the calculation function 153 calculates each "amplitude difference" on all of the pixels included in the area "R1" in the ultrasonic image. The calculation function 153 then calculates the rate "47.0%" of the shadows of "amplitude difference: 5 to 7," the rate "21.4%" of the shadows of "amplitude difference: 7 to 9," and the rate "5.04%" of the shadows of "amplitude difference: equal to or higher than 9." The control function 152 then causes the display 2 to display thereon the information about the relevant disease based on the above-described rates calculated by the calculation function 153.

The relevance between the rates of shadows and the disease is defined in advance and stored in the internal storage circuitry 16. In one example, the internal storage circuitry 16 stores therein "disease A," "disease B," and "disease C" as the disease relevant to a case in which the rate of shadows of "amplitude difference: 5 to 7" exceeds "50%." The internal storage circuitry 16 further stores therein "disease D" and "disease E" as the disease relevant to a case in which the rate of shadows of "amplitude difference: 7 to 9" exceeds "20%." The internal storage circuitry 16 stores therein "disease F" as the disease relevant to a case in which the rate of shadows of "amplitude difference: equal to or higher than 9" exceeds "10%." In this manner, the internal storage circuitry 16 stores therein the information on diseases defined in advance in accordance with the rates. The information on diseases stored in the internal storage circuitry 16 is stored by the operator as appropriate. That is, the relevance between the rate of the shadows and the disease is defined as desired by the operator. The above-described example is merely one example, and in addition to that, the disease and various rates of shadows are stored being associated with one another. For example, the rates and disease are stored being associated with one another, not only on "amplitude difference" but also on "width" and "pattern."

As for the relevance between the disease and the rate of shadows, it may be a case of being used in combination on the shadows as appropriate. In one example, it may be a case in which "disease A" is associated with, as the disease when the rate of shadows exceeded "50%" and the rate of the shadows of "amplitude difference: 7 to 9" exceeded "20%." In the same manner, it may be a case in which "disease G" is associated with, as the disease when the rate of "pattern A" exceeded "50%" and the rate of "pattern B" fell below "10%."

When the rates are calculated by the calculation function 153, the control function 152 refers to the information on diseases stored in the internal storage circuitry 16, and causes the display 2 to display thereon the information. For example, when the rate "47.0%" of the shadows of "amplitude difference: 5 to 7," the rate "21.4%" of the shadows of "amplitude difference: 7 to 9," and the rate "5.04%" of the shadows of "amplitude difference: equal to or higher than 9" are calculated by the calculation function 153, the control function 152 causes the display 2 to display thereon "disease D" and "disease E" as the information about a relevant disease because the rate of the shadows of "amplitude difference: 7 to 9" is exceeding "20%." The above-described example is merely one example, and in addition to that, the control function 152 can display the information about the relevant disease on various rates. For example, the control function 152 can cause the display 2 to display thereon the information about a relevant disease based on the rates calculated on "width" of the shadows and "pattern" of the shadows.

In the above-described embodiments, the situations in which the ultrasonic diagnostic apparatus performs the processing have been explained. The embodiments, however, are not limited to this, and it may be a situation in which the processing is performed by an image processing apparatus, for example. In ouch a case, the image processing apparatus include the above-described processing circuitry 15 and the internal storage circuitry 16, and executes the image generation function 151, the control function 152, and the calculation function 153. For example, the internal storage circuitry 16 stores therein the result of the ultrasound scan performed for a subject, and the computer programs corresponding to the image generation function 151, the control function 152, and the calculation function 153. The processing circuitry 15 then reads out the computer programs corresponding to the respective functions and executes the rad computer programs, and thereby performs the extraction processing of shadows on the result of the ultrasound scan stored a the internal storage circuitry 16.

The various constituent elements of the various devices and apparatuses illustrated in the explanation of the above-described embodiments are of functionally conceptual, and do not necessarily need to be configured physically as illustrated. That is, the specific forms of distribution or integration of the devices and apparatuses are not limited to those illustrated, and depending on various types of loads, usage conditions, and others, the whole or a part thereof can be configured by being functionally or physically distributed or integrated in any desired unit. Furthermore, the whole of or a part of the various processing functions that are performed in the various devices and apparatuses can be implemented by a CPU, and a computer program executed by the CPU, or be implemented as hardware by wired logic.

The processing method described in the foregoing embodiments can be implemented by executing a processing program prepared in advance on a computer such as a personal computer and a workstation. This processing program can be distributed via a network such as the Internet. The processing program can also be recorded on a computer-readable non-transitory recording medium such as a hard disk, a flexible disk (FD), a CD-ROM, an MO, a DVD, a USE memory, and a flash memory such as an SD card memory, and executed by being read out from the non-transitory recording medium by the computer.

As explained in the foregoing, according to the embodiments, the extraction of shadows in an ultrasonic image can be performed accurately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
processing circuitry configured to
cause an ultrasonic probe to perform an ultrasound scan of a subject;
detect a plurality of acoustic shadows by, in a result of the ultrasound scan, comparing a threshold value with a value based on a signal obtained by the ultrasound scan;
calculate, for each of the plurality of acoustic shadows, a respective at least one of a width and amplitude difference;
classify the plurality of acoustic shadows into a plurality of appearance patterns based on the respective at least one of the width and the amplitude difference for the plurality of acoustic shadows; and
generate a shadow image in which at least one of hue, saturation, and lightness is changed based on the plurality of appearance patterns of the plurality of acoustic shadows.

2. The ultrasonic diagnostic apparatus according to claim 1, wherein the processing circuitry is further configured to compare the threshold value with the value based on the signal for each depth; and generate shadow information that is information concerning the plurality of acoustic shadows based on comparison results for each depth, the shadow information including the widths and the amplitude differences of the plurality of acoustic shadows.

3. The ultrasonic diagnostic apparatus according to claim 1, wherein the processing circuitry is further configured to generate a superimposed image in which the shadow image is superimposed on a morphologic image based on the result of the ultrasound scan.

4. The ultrasonic diagnostic apparatus according to claim 2, wherein the processing circuitry is further configured to perform a measurement concerning the plurality of acoustic shadows based on the shadow information.

5. The ultrasonic diagnostic apparatus according to claim 4, wherein the processing circuitry is further configured to measure a rate of the plurality of acoustic shadows occupying the result of the ultrasound scan.

6. The ultrasonic diagnostic apparatus according to claim 2, wherein the processing circuitry is further configured to generate the shadow information by performing, at least one of a first comparison between a first threshold and each value corresponding to each signal obtained in an identical depth direction and a second comparison between a second threshold and each difference value between each value corresponding to each signal obtained in an identical depth direction and a reference value.

7. The ultrasonic diagnostic apparatus according to claim 6, wherein the processing circuitry is further configured to calculate, as each value corresponding to each signal obtained in the identical depth direction, each difference value between an average value of signal values of signals obtained in the identical depth direction and each signal value of the signals.

8. The ultrasonic diagnostic apparatus according to claim 6, wherein the processing circuitry is further configured to generate the shadow information after having applied a smoothing filter in a depth direction to signals obtained by the ultrasound scan.

9. The ultrasonic diagnostic apparatus according to claim 2, wherein the processing circuitry is further configured to generate the shadow information by performing a comparison between an amplitude of a reflected wave signal and a plurality of thresholds to analyze the reflected wave signal.

10. The ultrasonic diagnostic apparatus according to claim 4, wherein the processing circuitry is further configured to
measure a rate of the acoustic shadow occupying the result of the ultrasound scan; and
provide information about a relevant disease based on the measured rate of the acoustic shadow.

11. An ultrasonic diagnostic apparatus, comprising:
processing circuitry configured to
cause an ultrasonic probe to perform an ultrasound scan of a subject;
extract, at an identical depth, a plurality of values in a lateral direction in a two-dimensional ultrasonic image obtained by the ultrasound scan;
perform an analysis to identify a position where an acoustic shadow is generated at the identical depth by comparing a threshold with the plurality of values, a corresponding threshold being set for each of a plurality of depths; and
generate shadow information that is information concerning the acoustic shadow that has appeared in the two-dimensional image, based on a result of the analysis at the plurality of depths.

12. An image generating method, comprising:
acquiring a result of an ultrasound scan of a subject;
detect a plurality of acoustic shadows by, in a result of the ultrasound scan, comparing a threshold value with a value based on a signal obtained by the ultrasound scan;
calculating, for each of the plurality of acoustic shadows, a respective at least one of a width and amplitude difference;
classifying the plurality of acoustic shadows into a plurality of appearance patterns based on the respective at least one of the width and the amplitude difference for the plurality of acoustic shadows; and
generating a shadow image in which at least one of hue, saturation, and lightness is changed based on the plurality of appearance patterns of the plurality of acoustic shadows.

13. The image generating method according to claim 12, further comprising:
comparing the threshold value with the value based on the signal for each pth; and
generating shadow information that is information concerning the acoustic shadow that has appeared in the result of the ultrasound scan based on comparison results for each depth, the shadow information including the widths and the amplitude differences of the plurality of acoustic shadows.

14. The image generating method according to claim 13, wherein generating the shadow image based on the generated shadow information further comprises generating the shadow information by performing, at least one of a first comparison between a first threshold and each value corresponding to each signal obtained in an identical depth direction d a second comparison between a second threshold and each difference value between each value corresponding to each signal obtained in an identical depth direction and a reference value.

15. The image generating method according to claim 14, further comprising calculating, as each value corresponding to each signal obtained in the identical depth direction, each difference value between an average value of signal values of signals obtained in the identical depth direction and each signal value of the signals.

16. The image generating method according to claim 14, wherein generating the shadow image based on the generated shadow information further comprises generating the shadow information after having applied a smoothing filter in a depth direction to signals obtained by the ultrasound scan.

17. The ultrasonic diagnostic apparatus according to claim 1, wherein the processing circuitry is further configured to calculate, for each of the plurality of acoustic shadows, the respective amplitude difference, and
wherein the processing circuitry is further configured to classify the plurality of acoustic shadows into the plurality of appearance patterns based on the respective the amplitude differences for the plurality of acoustic shadows.

* * * * *